(12) United States Patent
Schwarz

(10) Patent No.: US 6,975,404 B2
(45) Date of Patent: Dec. 13, 2005

(54) DEVICE AND PROCESS FOR THE DETERMINATION OF THE PROPERTIES OF REFLECTIVE BODIES

(75) Inventor: Peter Schwarz, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 382 days.

(21) Appl. No.: 10/140,385

(22) Filed: May 6, 2002

(65) Prior Publication Data

US 2002/0167669 A1 Nov. 14, 2002

(30) Foreign Application Priority Data

May 11, 2001 (DE) .................. 101 22 917

(51) Int. Cl.$^7$ ............................. G01N 21/47
(52) U.S. Cl. ........................................ 356/446
(58) Field of Search ................ 356/600, 445–448

(56) References Cited

U.S. PATENT DOCUMENTS 4,479,718 A * 10/1984 Alman .................. 356/405
4,711,580 A * 12/1987 Venable ................ 356/446
5,583,642 A * 12/1996 Nakazono ............. 356/405

* cited by examiner

Primary Examiner—Richard A. Rosenberger
(74) Attorney, Agent, or Firm—Greer, Burns & Crain, LTD

(57) ABSTRACT

A device for determining the properties of reflective bodies has at least one illuminator that emits light onto a measurement surface, at least one detector for recording the light reflected from the measurement surface, the at least one detector includes a plurality of light-sensitive sensors. Substantially each sensor issues a measurement value characteristic of the light received by each respective sensor. Also included is at least one memory, having at least one first predefined threshold, at least one controller for the measurement sequence which includes at least one processor, whereby a measurement sequence is controllable such that a measurement value of a sensor is allocated to a first surface type when same exceeds the first threshold, wherein at least two sensors are respectively associated with different locations to be measured on the measurement surface, and wherein the controller is configured to issue at least one surface characteristic statistical parameter.

83 Claims, 8 Drawing Sheets

DEVICE AND PROCESS FOR THE DETERMINATION OF THE PROPERTIES OF REFLECTIVE BODIES

BACKGROUND OF THE INVENTION

The present invention relates to a device and process for determining the properties of reflective bodies and especially of heterogeneous reflective bodies. The visual characteristics of a body, respectively of a surface are, in a number of products, an important feature for the product's overall appearance. In order to achieve a high reproducibility during manufacturing or in the repairing of objects, measurements are thus made on prototypes or products for purposes of quality control in which one or several parameters are determined.

Particularly with finished surfaces, but not limited solely thereto, their visual properties may change depending upon viewing angle or angle of illumination. Such surfaces are called goniochromatic. Examples of such surfaces are those with effect, metallic or pearl lustre finishes, coated surfaces with interference color surfaces, or other synthetic surfaces or bodies having inlaid transparent or reflective particles or the like.

Heterogeneous reflective bodies include, for example, finished surfaces with inlaid metallic particles. Such surfaces are often smooth and unstructured.

Surfaces may exhibit, for example, so-called FLOP effects so that a change in color or gloss dependant upon the viewing angle may be observed.

Such effects may be induced, for example, by inlaid aluminum particles embedded in the surface or in the body itself and which then act as reflective material inclusions.

Measuring devices which illuminate a measurement surface at an angle and which measure the light reflected at, for example, two fixed angle ranges in order to determine the color of a surface to be appraised under these two scanning angles are known from the prior art.

Furthermore, goniometric measuring devices are also known in the prior art with which, for example, a surface is illuminated at a fixed angle and a movable photosensor is trammed across the entire angle range in order to obtain the surface color as a function of the scanning angle.

It is the task of the present invention to provide an improved device and an improved process of the type as indicated above for the determining of at least one property of a heterogeneous reflective body.

A further aspect of the task of the present invention is to provide a device which can determine at least one statistical property of a heterogeneous reflective body.

This task is solved in accordance with the present inventive device. The inventive process is also disclosed.

Preferred embodiments of the invention will also be described.

SUMMARY OF THE INVENTION

A device according to the present invention for determining the properties of heterogeneous reflective bodies comprises at least one illuminating means with which light can be radiated onto a measurement surface.

At least one detecting means is provided with which at least a portion of the light reflected from the measurement surface can be measured. At least one of the at least one detecting means includes a plurality of light-sensitive sensor means, whereby a measurement value is determined in substantially each of these sensor means, preferably separately, which is characteristic of the light received by each respective sensor means.

The inventive device has at least one memory means including at least one first predefined threshold. While the threshold is preferably stored as a fixed threshold, it may be altered by the user.

At least one controlling means serves to direct the measurement sequence and comprises at least one processing means which is preferably configured as a conventional microprocessor. The controlling means allows for the control of the measurement sequence such that a measurement value of a sensor means is allotted to a first surface type when the measurement value exceeds the first threshold. The controlling means is configured to determine at least one statistical parameter which characterizes the first surface type.

The device according to the present invention has numerous advantages.

These advantages will be described in the following with respect to heterogeneous reflective bodies. They also relate in correspondingly applied fashion to other bodies and surfaces.

When measuring heterogeneous reflective bodies in which, for example, effect pigments, metallic or aluminum particles or the like are inlaid in the surface or in the body itself, the distribution of the particles, pigments or the like plays a fundamental role in the visual appearance of the surface.

In order to appraise such a body or such a surface, the determination of a statistical distribution of a first surface type which can, for example, characterize the pigment reflection, is advantageous.

A preferred embodiment of the invention provides for a second predefined threshold, wherein preferably a measurement value is allotted to a second surface type when the measurement value falls below the second threshold. It is also possible for a second surface type to be allotted measurement values which are lower than the first threshold. It is likewise possible to divide the range of measurements into at least three segments. When a second predefined threshold is less than the first predefined threshold, three ranges for classification could ensue.

The classifying of surfaces into at least two surface types is advantageous because this allows for a more precise determination of the statistical properties of bodies or surfaces.

In a preferred embodiment of the present invention, the sensor means of at least one detecting means is arranged in rows and/or columns. In this case, it is preferred that the sensor means of a detecting means be arranged on a common substrate. It is further preferred that at least one detecting means is configured as a CCD array (charge-coupled device) or comprises one or more lines of diodes which offers the advantage, among others, that a very high number of sensor means can be provided.

Preferably at least one part of the sensor means of at least one detecting means is allocated to a respectively different location to be measured on the measurement surface. Mapping of at least one section of the measurement surface on the sensor means of at least one detecting means is particularly preferred.

Detecting means having up to several million sensor means are known today. Employing detecting means having a plurality of thousands or even more sensor means enables a high spatial resolution over the measurement surface. This allows for determining measurement values and parameters of a high locational resolution.

A preferred embodiment of the present invention provides for at least one-third threshold and at least one-third surface type as well as for the allotting of a measurement value to the surface type.

In a preferred embodiment, at least one statistical parameter for the statistical portion of at least one surface type on the measurement surface can be determined. This enables the separate determining of the percentile share of one or several surface types on the measurement surface across the entire measurement surface or over a subsection of the measurement surface.

In this way, statistical parameters can be derived as to the locational distribution of at least one surface type or one measurement surface.

This is advantageous because the spatial distribution of effect pigments, metallic particles like aluminum inclusions or so-called flakes are of great significance for the visual appearance of a measurement surface, a heterogeneous reflective body respectively.

Preferably a plurality of surface sections are derivable from the measurement values. Measurement values of neighboring sensors having the same surface type are allotted to the same surface section. Deriving a plurality of surface sections thus allows for determining the distribution of the respective types of surfaces.

A statistical parameter is then preferably derived from the surface sections of at least one or all surface types for the surface section particle size distribution relative the respective surface type. This is a very advantageous type of determination because particle size distribution of, for example, highly reflective surfaces, likewise plays a role in influencing the visual properties of a surface. A parameter for the particle size distribution facilitates the classification and appraisal of such surfaces.

In a preferred embodiment of the present invention, a statistical parameter for the spatial distribution of a surface section of (at least) one surface type on the measurement surface is derived from the surface sections of the (at least) one surface type.

It is preferable for a mapping property of at least one detecting means to be modifiable so that a section of the measurement surface can be depicted as an enlarged image. Preferably the detecting means can be zoomed in for this purpose. It may also be that, for example, a lens is arranged to be displaceable relative to the surface so that the mapping scale may be altered.

The enlargement of a section of the measurement surface is highly advantageous since this makes the finer structures observable at a better resolution. While larger structures can be examined at a smaller mapping scale, finer structures can then be examined statistically in an enlarged detail during a second step (or even more steps).

The visual properties of heterogeneous reflective surfaces can change significantly with the mapping scale. One only needs to think of, for example, color prints or color posters in which the individual colors are created by means of juxtaposition of a plurality of color dots in the primary colors.

A viewer only gets the integral impression at a greater distance while at close proximity, the individual dots are perceptible. The integral impression of the secondary colors comes through at a greater distance while the respective dots define the quality when viewed at less of an observation distance.

In another preferred embodiment of the present invention, at least one visual characteristic of the body to be examined can be determined which characterizes at least one visual property of the measurement surface. This visual characteristic may be one of any parameters as known in the prior art; in particular, it is preferable to be able to determine the gloss, color, haze, distinctness of image (DOI) or a measure of the surface ripple/orange peel, etc. Being able to determine at least two or more different visual characteristics of the measurement surface is particularly preferred.

Likewise particularly preferred is that at least one visual characteristic can be determined separately for at least one surface type, whereby it is preferred that the determination of the visual characteristic for a certain surface type transpires on the surface section of the corresponding surface type. An integral determination may also be carried out.

It is also preferred that at least one visual characteristic for at least one surface section of at least one surface type transpires separately. Especially preferred is that a visual characteristic is determinable for a plurality of surface sections of a surface type so as to also allow the deriving of a statistical distribution of the visual characteristics over the surface section of a surface type.

Preferably, the sum of the total number of detecting means and the total number of illuminating means amounts to 3, 4, 5, 6, 7, 8, 9, 10 or more, and the total number of detecting means is 1, 2, 3, 4, 5, 6 or more than 6. There are preferably at least 2, 3, 4, 5, 6, 7, 8, 9, 10 or more illuminating means provided.

A higher number of illuminating and/or detecting means allows for a higher resolution.

In a preferred embodiment, at least one second detecting means and/or at least one second illuminating means is arranged outside of a first measuring place, whereby the first measuring plane extends through a first illuminating means, a first detecting means and the measurement surface. It is hereby preferred for the second detecting means and/or the second illuminating means to be arranged at a predefined azimuthal angle or also a dihedral angle to the first measuring plane.

The arranging at least one detecting and/or illuminating means outside of the first measuring plane enables three-dimensional ascertaining of the measurement surface. This is of great advantage since many heterogeneous reflective bodies/surfaces have visual properties which not only vary in just one plane, but also across the steradian. The three-dimensional measuring of such a surface can be of importance to its appraisal.

Preferably, the illuminating means and the detecting means are respectively arranged at a predefined angle of height to the measurement surface and in such a way so as to enable a three-dimensional measuring of the surface.

In an advantageous embodiment of the present inventive device, at least one measuring device is provided which encompasses at least one illuminating means and at least one detecting means.

The measuring device can then emit radiation onto the surface to be measured and the same measuring device can detect the radiation reflected by the surface. The detected radiation can be radiation which is reflected or scattered back at the same steradian as which it came. But it may also be radiation which was emitted by another illuminating means and reflected off the surface (also specular).

Preferably, the illuminating means of the measuring device emits radiation to the measurement surface at a predefined measuring device angle and the detecting means receives reflected radiation from the measurement surface at this same predefined measuring device angle.

In a preferred embodiment, the measuring device comprises at least one beam splitter.

A beam splitter in a measuring device can transmit or divert radiation emitted by the illuminating means to the measurement surface.

Advantageous is the arranging of a beam splitter such that the radiation received by the measuring device from the measurement surface is conveyed or transmitted to the detecting means of the measuring device.

Especially preferred is for the same beam splitter to direct the light from the illuminating means onto the measurement surface and then direct the radiation received to the detecting means.

In one or all of the configurations of the present invention described above, a detecting means, respectively a reference detecting means, can be provided which controls the light emitted by at least one illuminating means. This enables a performance analysis of the illuminating means. A spectral effectivity control of the emitted radiation may also ensue. Conceivable hereto is the use of a filter wheel device, a breaking or bending or also a grid spectrometer, as well as the use of separate color filters.

Preferably, the controlling means allows the measuring sequence to be controlled in such a manner that at least a portion of the illuminating means can be triggered substantially successively during one measurement procedure so that the light emitted by the individual illuminating means can be measured separately by the respective detecting means.

This type of measurement is advantageous because the reflections yielding from the different illuminating means do not overlap one another but rather the measurement signals for each illuminating means are acquired separately.

This is advantageous, for example, when—contingent upon the special geometry—the signal of one illuminating means is especially strong on one sensor means. A correspondingly low amplification can then be selected for the measurement of this illuminating means. Then, when measuring the signal of other illuminating means, a correspondingly higher amplification is selected so that the signal-to-noise ratio, the resolution respectively, is as a whole higher.

Preferably a controlling means can also control a measurement procedure such that at least a portion of the one or also all of the illuminating means are triggered substantially simultaneously. Then the light emitted by the illuminating means can be acquired by the detecting means at the same time.

It is also possible that the one or other illuminating means are triggered in a staggered manner over time while, contingent upon the measuring conditions, a certain number of illuminating means are triggered simultaneously.

In a preferred embodiment of the present invention, the device's angle of touchdown on the measurement surface is variable. Different touchdown angles on the surface likewise allow for the performing of two-dimensional or also three-dimensional surface measurements, even should all of the illuminating means and detecting means be arranged substantially in one plane.

A three-dimensional measurement of this type is then namely possible when the device is tipped in a plane perpendicular to the measuring plane. The angle of touchdown can then be varied continuously or also at predetermined gradations. Changing of the angle of touchdown can be performed automatically or manually, whereby the touchdown angle is preferably (automatically) measurable.

It is also possible to, for example, manually set the device down on the body to be measured and then manually tram through a range of angles.

In a preferred embodiment, at least one parameter can be respectively determined for at least two or more different measurement geometries. A measurement geometry hereby being characteristic of the respective illuminating and respective measuring angle. A measurement geometry can thus, on the one hand, be generated by different illuminating angles and, on the other hand, by differing detecting angles. It is possible that one or more visual or statistical parameters are determinable for the different measurement geometries.

It is preferred hereto that at least one respective statistical parameter can be derived for at least two, three or more measurement geometries. This may be, for example, the statistical distribution of the first surface type over different measurement geometries. It is especially preferred that a statistical distribution of at least one statistical or visual characteristic of at least one surface type can be derived for a plurality of measurement geometries.

This type of determination is particularly advantageous since the number of, for example, flakes, effect pigments or reflective particles in the surface of the body can be acquired from the illumination angle or also from the detection angle.

Such an analysis is very advantageous in many cases since the arrangement of effect pigments and such within a body's surface or within a finish takes on great significance as far as the impression of color.

On the one hand, there are bodies in which metallic particles or the like are present as material inclusions and which act like mirrors. The distribution of such mirrors across the angle to the surface can be limited here to a narrow range of angles or even be distributed completely randomly.

In both cases, an analysis of the statistical distribution is greatly desired in order to, on the one hand, assess the quality of the body or the surface and, on the other hand, to be able to draw conclusions about the production process.

Preferably, two, three or more illuminating means and/or two, three or more detecting means are provided which are arranged substantially in a plane perpendicular to the measurement surface.

Preferably, two, three or more illuminating means and/or two, three or more detecting means are provided which are arranged preferably at different angles to the measurement surface. This type of arrangement enables a two-dimensional or also three-dimensional measurement of the body/measurement surface to be examined.

Preferably, different dihedral angles of the illuminating/detecting means are realized in a plane parallel to the measurement surface. In this way, some illuminating/detecting means could be arranged at different angles in a plane parallel to the measurement surface. The various different illuminating/detecting means could also be arranged such that the respective beams in one projection on a plane parallel to the measurement surface have different angles. The above-cited arrangement, in which the detecting and illuminating means are arranged three-dimensionally, allows for the achieving of improved readings.

It is also especially preferred to have at least one of the detecting means configured as a color LCD chip or the like in order to enable a direct color measurement or at least a color estimation.

But it is also possible for at least one detecting means to comprise three CCD chips or the like. Beam splitters in the detecting means can divide incident radiation among the individual CCD chips. The individual measuring chips are disposed with different color filters so as to enable a measurement of the color of the incident light reaching the detecting means.

In a preferred embodiment of one or more embodiments, preferably at least one iris means is arranged in the path of the ray between at least one illuminating means and at least one detecting means. Hereto, at least one iris means may be arranged between the illuminating means and the measurement surface and/or between the measurement surface and the detecting means.

It is likewise possible to dispose a first iris means between the illuminating means and the measurement surface and at least one second iris means between the measurement surface and the detecting means.

It is especially preferred to arrange substantially one iris in each case between each source of radiation and the measurement surface.

It is particularly preferred that at least one iris means has a variable and preferably controllable iris aperture.

The variable iris means may have a controllable aperture of dotted, slotted, linearly-shaped and/or rounded profile or other similar profile. It is particularly preferred to have at least one linear-type control of the iris aperture possible. In this regard, a mechanically operated slit is also possible.

It is especially preferred that at least one controllable iris means is configured as an electrically controllable iris means, and, particularly preferred, as an LCD or similar aperture means. It is particularly preferred that the iris means is operative during transmission and that the transmittance property of specific individual sections thereof can be controlled or switched off.

A controllable iris means, especially in the path of light between the illuminating means and the measurement surface is highly advantageous. It allows for controlling the angle of illumination on the measurement surface in very small angular gradations in a particularly precise fashion.

If the surface is illuminated at only a small angle interval, embedded metallic particles will only reflect light to the detecting means at the corresponding angle interval. A minute variation in the angle of incidence in the range of <1°, 2.5° or 5° can result in a high resolution of the metallic particles over the angle of incidence. This is especially important when appraising bodies with embedded (metallic) particles where they are to have a virtually identical alignment.

On the other hand, a greater range of measurement angles is of advantage when measuring surfaces having randomly distributed inclusions.

In a further preferred embodiment of one or all of the previously described embodiments, at least one illuminating means comprises at least one light source which is configured as one of the many light sources known in the prior art. Same may be, for example, a conventional thermal emitter such as an incandescent, halogen, krypton, etc. radiation source, or a semiconductor or laser light source or the like. Gas-pressure bulbs and the like may also be employed.

In all of the embodiments, it is preferred to have at least one lens provided in the path of radiation between at least one source of radiation and the measurement surface in order to be able to have an effect on the divergence/convergence of the light to be radiated.

During a measuring, the surface can be mapped on the sensor, the detecting means respectively. It is also possible for the sources of radiation to be mapped on an iris means or on a/the detecting means.

The radiation as emitted can also be focused onto the measurement surface or the detecting means when measuring.

It is preferred to arrange at least one of the lenses or a part of a lens means to be displaceable in order to be able to vary the divergence/convergence of the radiation emitted. In a simple case, a lens is displaceable along the optical axis.

A controllable lens position is also particularly preferable in order to adjust the desired divergence or convergence or to emit parallel light, wherein the control thereof may also transpire automatically in order to, for example, carry out separate measurements at different focuses.

The providing of at least one iris means and at least one lens in substantially each illuminating means is of particular preference.

It is especially preferred to have the frequency of the light emitted from at least one illuminating means be controllable and in such a way that preferably the color of the emitted light can be changed in a precise manner. This can be realized by means of, for example, a continuously tunable laser. It is likewise possible to precisely control a thermal source of radiation in correspondence with its current/voltage characteristic in order to vary the color temperature of the radiation emitted.

A precise control of the frequency of the emitted light is very advantageous since the corresponding frequency, wavelength and/or color of the light can be taken into account when recording measurement values, enabling a measurement of color.

At least one filter means is preferably arranged in the path of radiation between at least one illuminating means and at least one detecting means which changes the spectral characteristic of the incident light in accordance with the filter characteristics.

The spectral characteristic of the filter means is preferably variable and, particularly preferred, precisely controllable.

In an advantageous embodiment of the present invention, at least one filter means encompasses a filter wheel means which is preferably mounted so as to be rotatable. The filter wheel means preferably exhibits various different spectral characteristics across it periphery, respectively over the filter wheel surface. Upon the transmission of radiation to a stationary spot, the transmittance characteristic changes when the filter wheel is rotated.

It is especially preferred that the periphery of the filter wheel is divided into a plurality of three or more different filter segments, each having different filter characteristics and/or colors.

It is preferred to provide for at least 3, 4, 5, 6, 7, 8 or more different filter segments.

The filter characteristic may also change continuously across the peripheral angle/from 0 to 360 degrees. Defined fixed angle segments offer the advantage of there being clearly defined filter characteristics at each point of the filter while with a continuously varying filter, the filter property is contingent upon the peripheral angle.

In a preferred embodiment of the present invention, at least one detecting means comprises sensor means of spectrally different sensitivity, whereby it is especially preferred to provide for at least three sensor means of spectrally different sensitivities. It is then preferential for the three sensor means of spectrally different sensitivities to measure the light from substantially the same measurement point on the measurement surface so that the color of the individual dots on the surface will be ascertainable even in relatively inhomogeneous surfaces.

It is often the case in the printing industry that posters, placards or color prints are generally only printed with a given number of primary colors. Secondary colors are produced by printing various color dots of different primary colors next to one another or also on top of one another.

Colors mixed by printing color dots next to each other gives a viewer the desired impression of color only upon sufficient distance therefrom. A viewer will (still) perceive the individual dots of color when observing from a lesser distance which will then fuse into a secondary color once a sufficiently great enough distance is reached. The necessary distance for this process depends upon the size of the individual color dots.

For purposes of quality control, it has become common practice in the printing industry to print a pattern of the primary color dots or even certain secondary colors on special areas of test prints or on predefined surfaces or places within a series print run.

The color dots are then arranged in a predetermined pattern respective one another. Measuring the colors of the individual printed dots or printed surfaces or also the distribution of color on the test pattern allows for making a determination of whether the printing machine is properly set and/or whether the printing is running with the proper colors or on the right, respectively precisely-defined substrate, because the resulting color depends not only on the colors as printed but also on the base material, etc.

Then, for purposes of quality determination and control during a print run, a test sheet can be measured following a predetermined number of sheets or interval of time or predefined printed surface. In this regard, it will then suffice to check the test pattern as simultaneously printed for its color composition.

The inventive device makes such a measurement very simple. The color of the individual printed dots can be determined quickly and reliably.

In one or all of the embodiments of the present invention, the first or even all of the thresholds can be defined to be color-sensitive so that a threshold (in the sense of a vector) will comprise, for example, three components for red, green and blue. Or different thresholds can be given for different colors or ranges of wavelength.

This type of color measurement transpires especially reliably particularly in an embodiment provided with a filter wheel means.

When measuring, a depiction of the test pattern to be measured can be filed to the memory means. Pattern comparison allows the corresponding area of the sensor means to be set to the detecting means. A particularly simple evaluation is then possible since all that is required is to compare each color dot of the test surface as to its actual measured dot color versus its associated set color.

When an absolute or relative color deviation and/or the total of all color deviations is exceeded, a parameter, alarm signal, indication or the like can issue.

In the case of a number of differently colored measurement points, each different color can characterize a surface type. A (respective) statistical parameter can then be determined for one, several or all surface types which characterizes the respective surface type.

In a preferred embodiment of the present invention, the device is displaceable relative to the measurement surface and at least one path measuring means is provided which quantitatively records this relative displacement. It is possible hereto to have the path measuring means be disposed as electric, mechanical or optical means.

The path measuring means preferably comprises at least one measuring wheel which is set down upon the surface to be measured during measurement and turns during the relative displacement of measurement surface to measuring device.

Preferably, the path measuring means includes at least one rotating angle emitter which emits an electrical signal representative of the relative displacement.

Measuring the displacement of the device relative the surface to be measured has many advantages. Ascertaining the relative displacement enables the repeating of surface measurements at given or openly variable intervals.

It is also possible to measure a large portion or even the entire surface so that the measurement surfaces of different measuring procedures can precisely follow one another. It is possible, for example, that a signal tone is emitted after the device has reached a certain displacement and the user can then perform another measurement procedure or that following the reaching of a certain relative displacement, the device automatically performs another measurement.

When measuring over a larger portion of the surface to be measured, statistical properties in particular can be determined better over the measurement surface. With a large-area measurement, it is often possible to detect a cloudiness in a finished surface which is caused during finishing when a spray nozzle lingers too long over one particular spot.

A frame device is provided in a preferred embodiment of the present invention on which the path measuring means is arranged. It is especially preferred for this frame device to be provided as a separate device and one which can receive the measuring device with illuminating and detecting means. If only single measurements are to be made, however, the frame device can remain separate from the other devices.

In a preferred embodiment of the present invention, the measurement surface on the body to be measured can be selected by changing the system angle, wherein it is also possible to vary the measurement surface on the body to be measured by, for example, varying the scanning angle.

It is likewise possible to provide a robot arm device which guides the optical measuring device to and preferably along the measurement surface. This allows for the automatic measuring of all components.

Preferably, successive measurements during a relative displacement, or the evaluated visual and/or statistical parameters respectively, are stored according to location so that a locationally-contingent evaluation of the measurements or the evaluated parameters can be performed.

In accordance with another preferred embodiment of one or more of the previously described preferred embodiments, at least one detecting means and at least one illuminating means are arranged such that at least one optical transmittance property of the measurement surface can be determined. The optical transmittance properties of this type of measurement surface are likewise an important factor for the visual impression of many heterogeneous reflective surfaces and bodies.

It is possible to provide a separate illuminating means which is movable on the other side of a test sample to be measured. It is likewise possible to provide for an insertion possibility, a slot or the like, in the inventive device so that a probe can be placed into the measuring device, respectively project into or through, for the purpose of determining at least one optical transmittance property of the measurement surface.

In another preferred embodiment of the present invention, a spectral filtering means is provided on at least one illuminating means which approaches a predetermined spectral distribution of the spectrum emitted by the illuminating means as, e.g., that as exhibited by a standard light type.

It is likewise possible that a spectral filtering means of this type be arranged in the path of radiation in front of the detecting means in order to reproduce the desired spectrum of an ideally reflective surface from the corresponding illuminating means.

It is especially preferred that at least one detecting means comprises at least one spectrometer or spectral device so that a spectral characteristic and in particular a spectrum of the received light can be ascertained.

Providing a plurality of retaining means is preferred in a further embodiment of the present invention which each may serve in the receiving of measuring or illuminating means while only a smaller number of measuring or illuminating means are actually provided. A greater number of retaining means than the total of illuminating and measuring means is advantageous in that it simply enables changing the position of a measuring means from a first retaining means to a second retaining means where no measuring or illuminating means had previously been disposed.

With this type of device, the individual positions of the measuring/illuminating means can be changed at substantially any time, which enables the adapting of the device to changing measurement conditions. It is preferred that the angular separation of the retaining means amounts to 2, 2.5, 3, 4, 5, 6, 10, 15, 20 or 30 degrees. The angular separation may also be smaller or greater. The measuring/illuminating means may also be arranged in a three-dimensional distribution such as, e.g. hemispherical or cube shape, etc.

It is preferred that an illuminating means and a detecting means are arranged at such an angle to the surface that the detecting means receives the light reflected directly by the surface from the corresponding illuminating means.

It is furthermore preferred that at least one illuminating means and/or detecting means is aligned at such an angle to the surface that the detecting means does not receive the directly-reflected light.

In another embodiment of the present invention, at least one retaining means is configured such that it is suited to receive an optical, device, whereby the optical device may be configured as a detecting means, illuminating means, measuring means, etc.

When an arbitrary optical device can be retained or received as such, this offers any number of expansion and customization possibilities to the invention.

There is preferably a plurality of such retaining means in at least one measuring plane which each exhibit the same angular separation to one another.

The angular separation can be between 0 and 45°, but is preferably between 1 and 5°.

For taking multi-dimensional measurements, an embodiment provides for disposing a second plurality of retaining means in at least one second measuring plane.

The source of radiation of at least one illuminating means of the device preferably exhibits a radiated spectrum which substantially covers at least the entire visible range of the spectrum. It is preferred to make use of light-emitting diodes, whereby the use of at least one white light light-emitting diode in the inventive device is especially preferred. Other light sources may also be employed.

A number of differently colored light-emitting diodes may also be employed which radiate light simultaneously with their radiations being overlapped. Several monochromatic light-emitting diodes may also be operated successively in order to perform a color measurement.

In all of the embodiments as described, at least one control measurement means may be provided to determine a standard measure for the light emitted by the illuminating means.

In addition, a temperature measuring means may also be provided which determines the temperature of the illuminating means and/or the detecting means during measurement. These measures allow for increasing the reproducibility of a measurement since fluctuations in the light intensity and/or temperature of the devices can be taken into account.

The inventive process, especially for the determining of the properties of heterogeneous reflective bodies, is performed employing a device which comprises at least one illuminating means and one detecting means. The illuminating means serves for radiating light onto the measurement surface and the detecting means is used for recording at least a portion of the light reflected by the measurement surface.

At least one detecting means includes a plurality of light-sensitive sensor means, whereby substantially each of the sensor means emits a respective measurement value which is characteristic of the light received by the respective sensor means.

At least one memory means is provided in the device and at least one predefined threshold is stored in the memory means.

At least one controlling means having at least one processing means serves to control the measurement sequence.

The inventive process is performed based on the following procedural steps, whereby the sequential order in which these procedural steps are performed does not necessarily have to follow the cited order but may also transpire in any other arbitrary sequential order provided that same would make sense.

The process comprises at least the following steps:
 a) directing of at least one illuminating means to light the measurement surface.
 b) directing of at least one detecting means, respectively the sensor means of at least one of the detecting means, to record the measurement signals of the sensor means of at least one detecting means and to convert same into measurement reference values.
 c) saving at least a portion of the recorded reference values to the memory means.
 d) comparing the magnitude of each measurement reference value with the first threshold stored in the memory means in order to allot each measurement value to a first surface type should the measurement value be greater than the first threshold.
 e) issuing of a statistical parameter which is characteristic for the first surface type.

The inventive process has many advantages.

In accordance with an embodiment of the inventive process, at least one second threshold is provided, whereby measurement reference values smaller than the second threshold are allotted to a second surface type. Allocations to a third surface type may proceed in like manner.

In one embodiment, the number of measurement reference values corresponding to the first surface type is determined and set in comparison with the number of measurement values as a whole.

The parameter preferably characterizes a statistical distribution of the first surface type.

In accordance with an embodiment, the process is performed making use of a device in which at least one detecting means substantially logs a map of the measurement surface so as to enable the determining of at least one statistical parameter of the statistical spatial distribution of the first surface type on the measurement surface.

The issuing of such a statistical parameter could, for example, be as a value between 0 and 1, whereby the value of 0 would then befit a particularly homogeneously spatial distribution while the value of 1 would refer to a high degree of localization.

Yet it is also possible for a higher value to describe a parameter of homogeneous distribution. This type of statistical evaluation is advantageous since the macroscopic homogeneity of the surface is important for its visual appearance.

In a preferred embodiment of the present invention, surface areas are derived for at least one or all surface types. The distension of each individual surface area transpires in that the measurement values of adjacent sensor means determine the same surface type. An individual section therefore directly describes a related area having the same surface type to the detecting means. Based upon the properties mapped by the detecting means, each surface area can be allotted to a defined section of the surface to be measured.

The size and position of the individual surface sections are preferably stored to the memory means. It is then preferential that the respective size is determined for substantially each of said surface sections. A determination of size can be done by a simple counting of the relevant sensor means. Additional statistical parameters may also be derived which are characteristic for a statistical size distribution of the surface sections of at least one surface type. A further possibility is the determination of the number of particles or the like per surface unit or their distribution of frequency.

In another preferential embodiment of the inventive process, at least one standard measure is determined for a form of surface area and preferably at least one statistical form parameter derived which is characteristic for a statistical form distribution for the surface areas of at least one surface type.

With, for example, substantially elongated material inclusions in the body to be measured or its surface, the form parameter may be a measure of the length distribution of individual material inclusions, while with material inclusions or particles which tend to be more rounded/rounded off or flat, the form parameter may be a measure of the roundness, etc.

In a preferred embodiment of the present inventive process, individual or all procedural steps are performed for at least two different measurement geometries. Hereto, a measurement geometry is defined by the angle of illumination to the measurement surface and the respective angle of detection to the measurement surface. Illumination and detection angles may in each case have an azimuthal angle and a height angle ratio.

Especially preferred is for the evaluation to transpire not with only two, but rather at three, four or a plurality of measurement geometries so that a statistical distribution of a visual or statistical parameter can be determined across the measurement geometries. This can be realized by, for example, aligning a plurality of illuminating means at different angles to the measurement surface.

In order to allow three-dimensional surface measurements, a preferred embodiment of the present invention arranges the illuminating means not just in one plane, but rather distributed within the space. It is in fact likewise possible to provide for a number of detecting means which are also not arranged in just one plane, but rather three-dimensionally.

In an embodiment of the inventive process, measurement values for the first surface type are allotted a first type of material inclusion for the body to be measured so as to determine a statistical parameter for the distribution of the material inclusions across the measurement surface, the body to be measured respectively.

In a variant of the measuring procedure, emitted radiation is focused on the measurement surface during measuring. In another configuration, substantially parallel light is radiated onto the measurement surface to be appraised.

In such manner, two measurement geometries can differ in their illumination/detection angles such that the detector can record a direct reflection of a certain flake or a certain material inclusion in the first geometry, while the directional reflection of the same flake or material inclusion would no longer be logged by the detector in another measurement geometry. Whether the directional reflection of a flake or the like would still be recorded by the detector in a second measurement geometry depends upon the shape and the size of the flake or material inclusion, etc., the difference in illumination/detection angle, the shape and the composition of the body to be examined, and various other factors.

Upon small or minute changes in the illumination/detection angle (e.g. on an order of magnitude of 0.1°), the directional reflection of one flake, for example, may feasibly still be able to be recorded on the detecting surface.

If, however, the illumination and/or detection angle is changed by a greater degree of angle, the directional reflection of the same flake will no longer be recorded. Instead, reflections of other material inclusions can be received and evaluated. This may be the case, for example, given conventional flakes and changes to the angle of illumination of 50. An evaluation of the three-dimensional form of inclusion would then feasibly only be possible to a limited extent.

The statistical evaluation of distribution over a two-dimensional surface, however, is quite important and also sufficient in many cases, and is also possible without any analysis of form. The visual appearance of surfaces depends to a great degree on a homogeneous distribution so that a statistical evaluation of the (two-dimensional) distribution over the measurement surface is very advantageous.

In the comparison of the surface sections at two, three or more differing measurement geometries in an embodiment of the process, a characteristic measure is derived for a three-dimensional form of the first material inclusion.

This can transpire in that, for example, with small changes in the illuminating angle (enabled, for example, by a controllable iris means), the displacement of individual surface sections when measuring under a first angle compared to the measurement under a second angle can be derived by means of an image analysis.

When individual surface areas remain roughly the same size at different angles, this indicates a flat structure to the material inclusions, while a decreasing or increasing size signifies a convex or concave form to the material inclusions. Round or spherical forms of material inclusions can also be determined using this manner of evaluation.

For the determination of form for individual color pigments or material inclusions or foreign matter, it is preferential that the angle of a measurement geometry only change to a small degree from one measurement to the next. This change can be in the range of one or several degrees of angle or even less.

For the appraising of material inclusions distributed randomly across all angular ranges in a body to be measured, the realizing of a large angular range for the illumination or detection is preferred in order to enable information to be received about the allocation over a large range of angles.

It is preferably possible with the inventive process that at least one characteristic visual parameter is determined for at least one surface type. Hereto, only measurement values of the respective surface type are considered when determining characteristic visual parameters. It is likewise possible when determining a characteristic visual parameter that only those measurement values be considered which are not related to a certain or to several certain surface types.

It is frequently the case with heterogeneous reflective bodies that a given color impression is substantially only elicited by a special surface type. This type of measurement process ensures that when measuring, substantially those surface sections of the surface to be measured which exhibit the corresponding surface type will be taken into account.

As an example, when considering a color or gloss parameter for surfaces provided with effect or pearl lustre pigments, metallic particles or the like, the corresponding surface type(s) can be omitted from consideration.

Aluminum or metallic inclusions often exhibit a high reflectivity which goes far beyond that of a typical surface gloss. If, when measuring color or gloss, the reflections of these particles are substantially not taken into consideration, the surface color can then be determined reliably.

It is furthermore preferred that one of the previously described configurations of the inventive device be employed when carrying out the inventive process.

Further advantages, features and application possibilities of the present invention will now be specified in the following description of embodiments in conjunction with the drawings.

DETAILED DESCRIPTION OF THE PREFERRED EMBODIMENT

A first embodiment will now be described in the following with reference to FIGS. 1 through 8.

Figure 1:
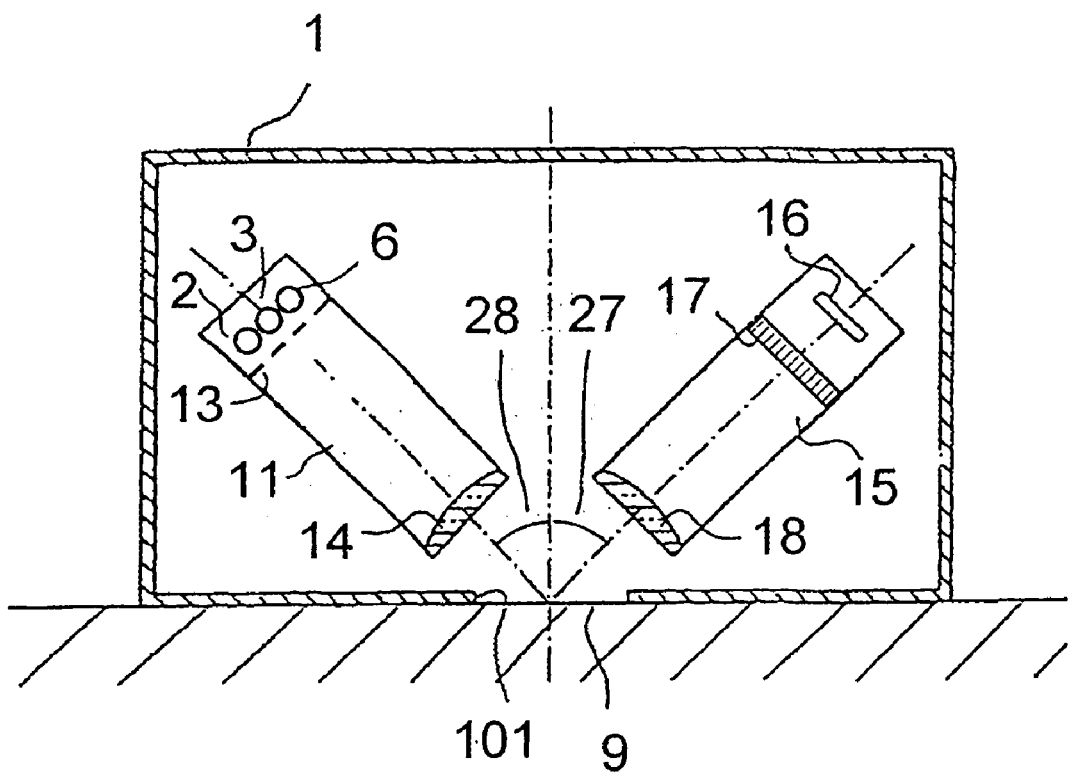
FIG. 1 is the principal construction of a device according to a first embodiment of the present invention in a side view.
Figure 2:
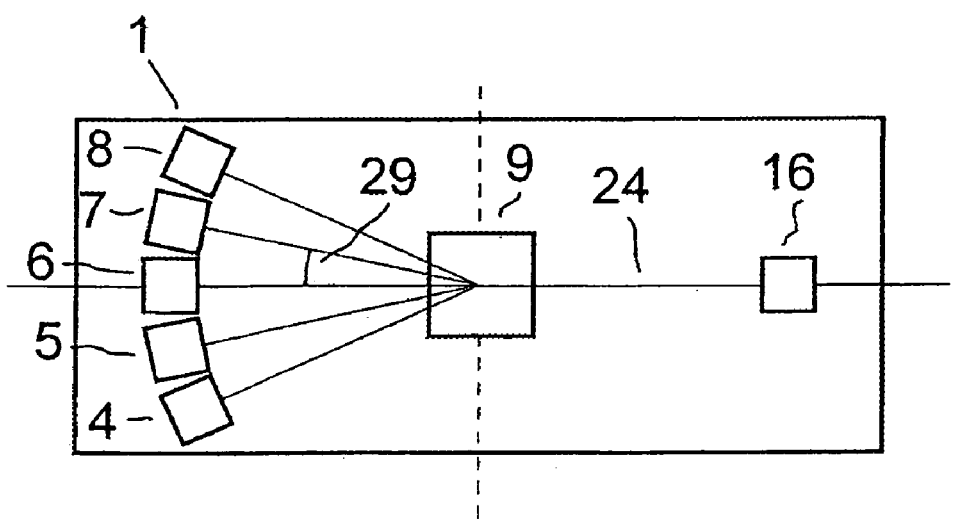
FIG. 2 is the principal construction of a device in accordance with FIG. 1 in a structural view from above.

FIG. 1 represents a cross-sectional view through a first embodiment of a device according to the present invention.

Several (here seven) illuminating means, respectively light sources 2, 3, 4, 5, 6, 7 and 8 are disposed in a housing 1 which direct light onto a measurement surface 9. There could also be fewer or notably more provided; e.g., 10, 12, 15, 20 or also just 4 or 6.

To limit the beam of light, a multi-iris 13 is provided which limits the respective beam of each light source. A lens 14 may be provided (or one separate lens is provided for each illuminating means or, also, in addition to lens 14 yet another lens is provided additionally for each respective illuminating means) to affect the divergence of the emitted light so that it is also possible to direct a substantially parallel beam of light onto measurement surface 9.

The individual illuminating means 2, 3 and 6 are aligned at different angles of height 28 to the measurement surface 9, while a detecting means 16 receives light reflected from the surface at a measurement angle 27.

The detector 16 is configured as a CCD chip, its individual photosensitive elements 30 arranged in plate-like rows 40 and columns 41. A lens 18 disposed in the path of radiation between the surface to be measured and the detector 16 serves to map the light sources or the measurement surface or a portion of same on the detector 16 or similar component.

Although it is not shown in FIG. 1, a greater number of detectors 16 may also be provided which may then be disposed, for example, to be directed at different angles to the measurement surface 9. In like fashion, more or fewer light sources 2–8 can also be provided.

Light sources 2, 3 and 6 configured as light-emitting diodes are arranged in a measuring plane 24. The measuring plane 24 is that plane which in the embodiment extends through the illuminating means 6, the measurement surface 9 and the detector 16.

Light-emitting diodes 4, 5, 6, 7 and 8 also configured as light-emitting diodes are arranged in a plane parallel to measurement surface 9 and perpendicular to the evenly defined measuring plane 24. The individual light-emitting diodes are arranged at different azimuthal angles to measuring plane 24.

Light-emitting diode 7 is also directed at the height angle 28 to measurement surface 24, however additionally exhibits an azimuthal angle 29 to measuring plane 24. This three-dimensional arrangement of light sources relative the measurement surface enables the three-dimensional mapping of measurement surface 9 in order to thus be able to determine the heterogeneous properties of the measurement surface in a more exacting and precise fashion.

A controllable iris 17 may be provided in the path of radiation between the light sources 2–8 and the detector 16. The controllable iris 17 is configured as an LCD iris in the present embodiment in which individual regions, lines, columns or pixels can be specifically controlled so that the specific controlling can limit the detector 16 to logging only certain ranges of angles from the measurement surface 9 while other remain shadowed or shaded.

The controllable iris 17 can also be arranged in the path of radiation between the illuminating means 2–8 and the measurement surface 9 so that the angle of illumination to the measurement surface can then be set in especially small gradations.

Controllable iris 17 has the advantage that images of surface 9 can be recorded at small and minutest changes of angle, allowing detection of small and minute changes.

In addition to light-emitting diodes 4–8, further sources of light or radiation can be provided at other angles of height or azimuthal angles 29 to measuring plane 24 in order to measure surface 9 from many different steradians.

Figure 4:
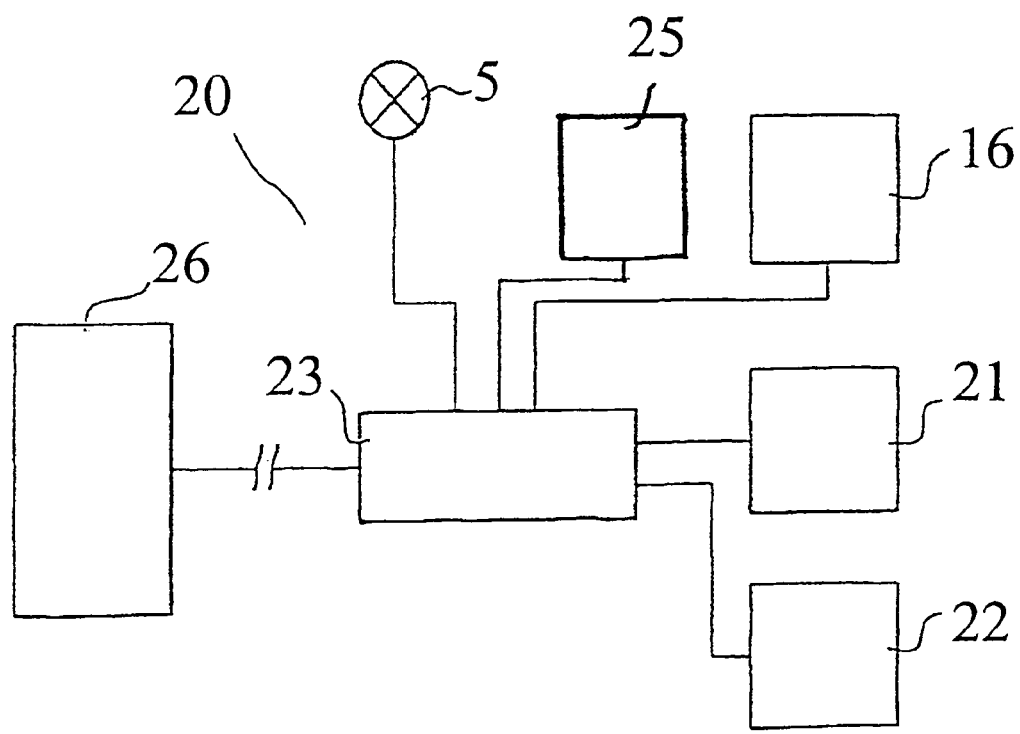
FIG. 4 is the principal technical circuitry configuration of the embodiment according to FIG. 1.

FIG. 4 shows the principal technical circuitry configuration of the inventive device. Controlling means 20 comprises a processing means 23 configured as a microprocessor, a memory 25, input and operating elements 21, and a display 22. The example depicts only one light source 5 and one CCD chip as detector means 16. The user can make a data connection to an external computer 26 via an interface.

Figures 6A, 6B:
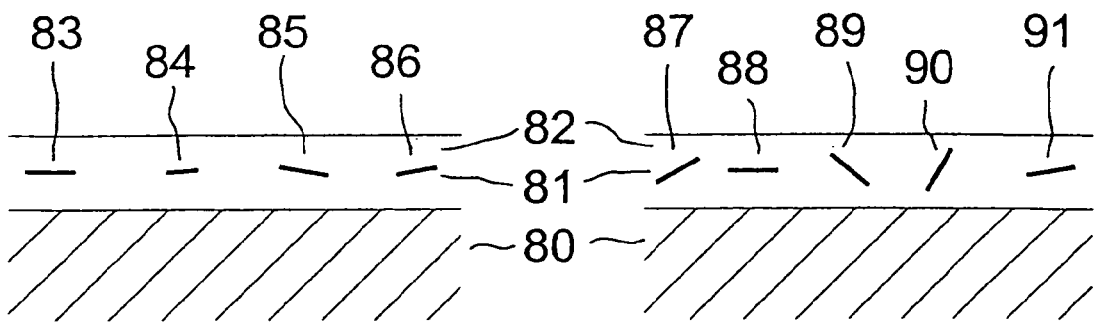
FIG. 6a shows material inclusions in a finished surface in a first example of a body to appraised.
FIG. 6b shows material inclusions in a finished surface in another example of a body to be appraised.

A measuring procedure for a first example of a heterogeneous reflective body 80, as represented by FIG. 6a, will now be explained in the following.

A finished surface 81 of the body 80 exhibits, in addition to a normal finish 82, a plurality of material inclusions 83–86 which in the selected example are configured as small reflective metallic wafers and are aligned substantially parallel to the surface in the selected example.

The normal finish 82 reflects a portion of the light impinging directly on the surface in correspondence with its color and other properties, while another portion penetrates the layer of finish. The light entering into the layer of finish may hit one of material inclusions 83–86 which will then effectively reflect this light.

When a beam of light is reflected by one of the material inclusions 83–86, the hue of the material inclusion substantially determines the color of this reflection. A beam of light which is reflected on the surface of the layer of finish 82 may exhibit another color and a clearly different intensity.

The color impression, the visual appearance respectively, of the overall surface is composed of the reflection on the surface of the finish and the reflection on the metallic particles 83–86. Overall appearance is, on the one hand, a mixture of different color impressions and, on the other hand, dependent upon the statistical distribution and also the statistical particle size distribution of the individual material inclusions 83–86. The impression is likewise contingent upon the distance and angle of observation.

While the human eye may conceivably not be able to distinguish separately between small and minute material inclusions in a surface, it can ascertain material inclusions having larger surface area as independent components. In the case of larger surface area components, the human eye is capable of perceiving not only one but two (separate) color impressions of a surface to be measured.

In such a case, the determination of an integral overall impression is not sufficient in making an assessment of the surface, rather it is important to determine a value for the visual property/properties for each respectively different type of surface (i.e., the normal layer of finish 82 and the material inclusions 83–86).

The overall visual appearance can thus be highly dependent upon the statistical distribution of material inclusions in the measurement surface and the statistical particle size distribution of these material inclusions within the measurement surface.

Included among the visual properties having an effect are, for example, the gloss, the color of the measurement surface, the haze, and also the impression of ripple to the surface to be examined as well as other visual properties known in the prior art for characterizing surfaces and familiar to the expert.

FIG. 6b depicts an example of another body 80 which likewise has a finished surface having a layer of finish 82. A plurality of material inclusions 87–91 are provided in this surface which, in contrast to those in the depiction according to the FIG. 6a representation, however, are distributed randomly and irregularly in their angular alignment to the surface.

Figure 3A:
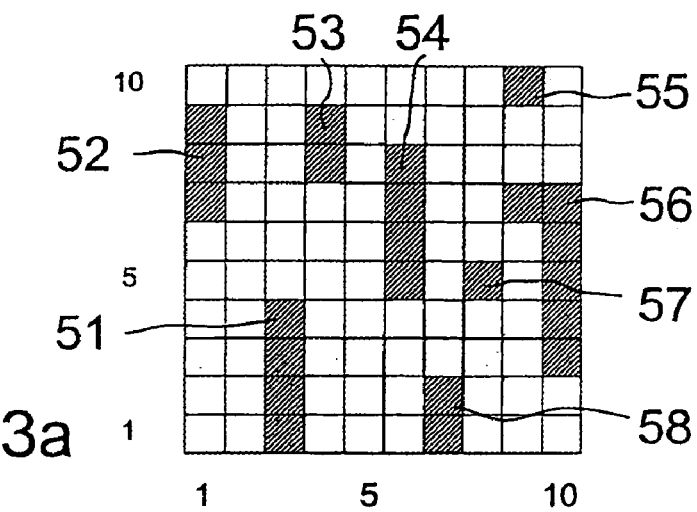
FIG. 3a is a representation of the distribution of a surface type across a detector surface at a first measuring angle.

FIG. 3a depicts a principal representation of detector 16, its individual light-sensitive elements 30 arranged in rows 40 and columns 41. Although there are only a total of 100 photo-sensitive elements depicted in FIG. 3 (10 per row, 10 per column), it is pointed out here that this is only a principle representation and that the detector employed in the embodiment is a conventional CCD chip which may have up to a few million different photo-sensitive surfaces.

For illuminating/mapping, the suitable transmission/reception optics are selected, whereby these may also be configured to be variable. In particular, the emitted light may be directed to be substantially parallel. Divergent or convergent radiation may be set for the (transmission) optics. There may be a bundling or also focusing on the measurement surface 9 or also on the iris 17 in the illuminating means or receiving optics.

To change the properties recorded, at least one lens of at least one light source can be arranged so as to be displaceable in order to, for example, enable a selective focusing onto the measurement surface 9 or onto the iris 17.

During measurement, measurement signals 33 are logged for the individual photo-sensitive elements 30 of CCD chip 16. A comparison of the individual measurement signals with threshold 32 stored in the memory determines whether the measurement value can be attributed to the normal finished surface 82 or to one of the highly reflective metallic particles 83–86. The detector elements associated with the example's surface type 81 are depicted in FIG. 3 as hatched areas 50.

The surface distribution represented in FIG. 3a was obtained at a first angle of illumination. The surface distribution represented in FIG. 3b was measured from a slightly different second angle of illumination relative the FIG. 3a reading.

Because of the slight changes in angle of illumination, individual surface areas 50, which are associated with the same highly reflective material inclusions, can be detected.

Figure 3B:
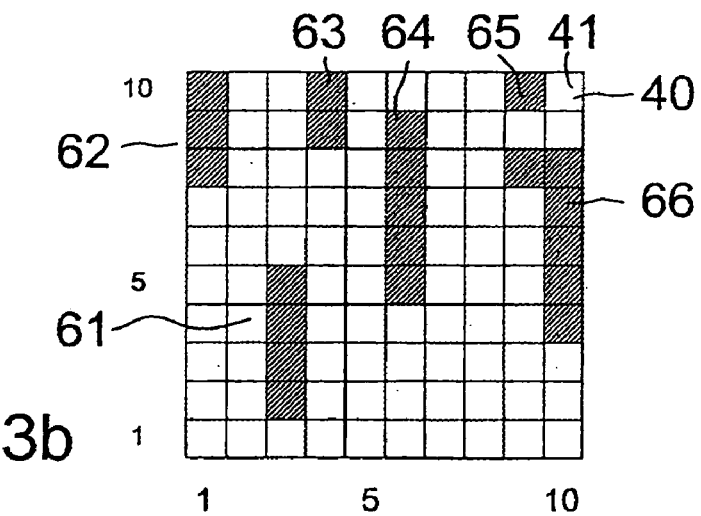
FIG. 3b is a representation of the distribution of a first surface type across a detector surface at a second measuring angle.

In this way, the material inclusion 83 in the surface section 51 of FIG. 3a will, for example, correspondingly lead to illuminating or sensor elements 1–4 in the third column. The measurement results for the slightly altered geometry in accordance with FIG. 3b show the reflection of material inclusion 83 now detectable on elements 2–5 of the third column. In exactly the same manner, a plurality of surface areas 52, 53 and 54 in the same column shift upward by one sensor element each, as does an L-shaped area pattern 56—also shifting upward by one sensor element 30 in the same columns 9 and 10.

In contrast thereto, area patterns 57 and 58 are no longer present in the measurement results in accordance with FIG. 3b. Area patterns 57 and 58 have no correspondence in the representation according to FIG. 3b. This is due to the fact that the related material inclusions do not reflect here to any considerable extent at the new angle of illumination according to FIG. 3b, respectively the detector no longer logs their reflection.

A surface area 55 (row 10, column 9) in FIG. 3a can have its correspondence in a surface area 65 (row 10, column 9) in accordance with FIG. 3b. The result of there not having been any sensor element changes upon changing of the angle is due to the change in angle being insufficient enough to cease in illuminating the corresponding sensor element.

In order to increase the accuracy of measurement results, not only one threshold 32 can be taken into account, but also the absolute magnitude of the measurement value can be considered in that, e.g., surface area 50 is not limited by threshold 32 but rather by a drop in a certain percentage of the maximum value lying below or above the threshold, etc.

Figure 3C:
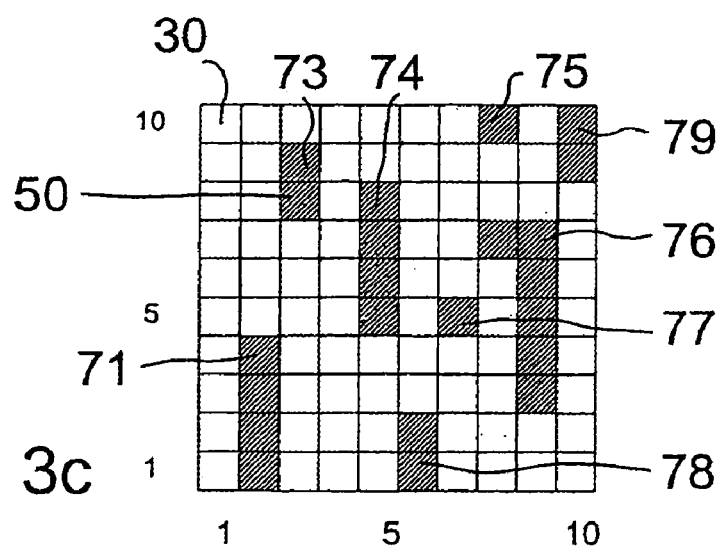
FIG. 3c is a representation of the distribution of a first surface type across a detector surface at a third measuring angle.

The individual surface areas 51–58 and a plurality of surface areas 61–66 as well as a plurality of surface areas 71 and 73–79 are determined in that for measurements of a given surface type 83–86, measurement values of the neighboring photosensitive elements are polled. Should these measurement values likewise fulfill the conditions (e.g. greater than threshold 32), this surface section will be enlarged accordingly so as to result in the surface area as represented in FIGS. 3a–3c.

A first evaluation result can be attained by means of a summation of the surface allotments of the first surface type in that the surface allotment of the first surface type is given in relation to the total surface.

Figure 5:
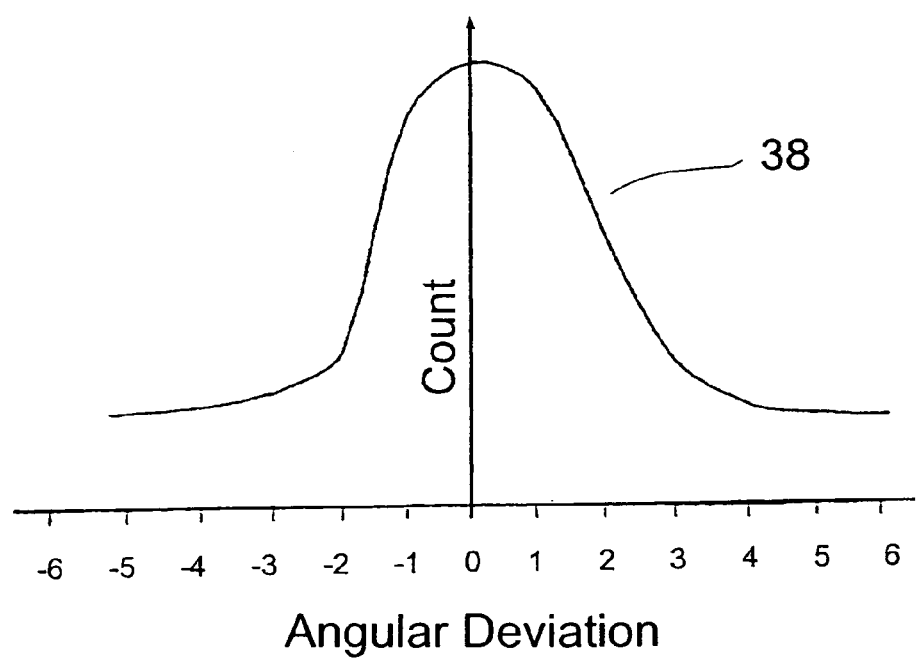
FIG. 5 is the progression of the surface allotment of the first surface type across the entire surface at the angle of illumination.

The statistical distribution of such a surface allotment across an illumination angle deviation is represented in FIG. 5 as surface allotment progression 38. The progression as depicted yields that the individual particles 83–86 are aligned at a narrow angular interval to the surface.

Figure 7:
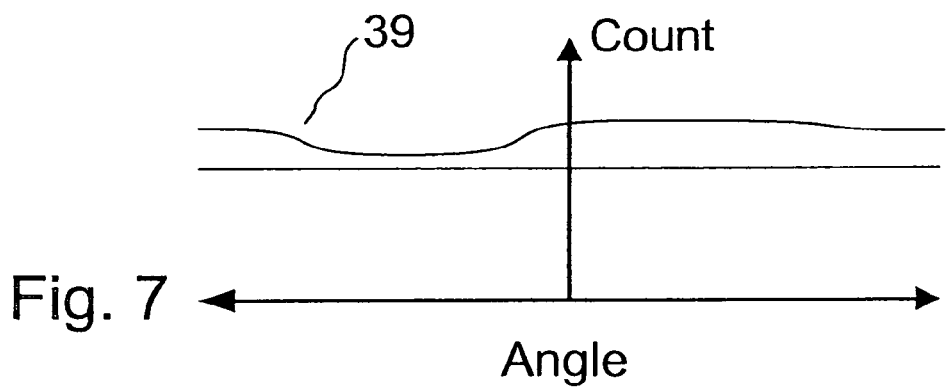
FIG. 7 is the homogeneity of a distribution of material inclusions across the angle of measurement.

Upon an irregularly aligned distribution to the individual material inclusions 87–91, as indicated in FIG. 6b, a distribution more like that as depicted in FIG. 7 will result. Here, the distribution 39 is substantially constant across the deviation in illumination angle.

The mapped properties ascertained for the transmission/receiving optics may also be adapted for measurements of this type of surface in that the position of the respective lens relative the light source/sensor is variable.

An evaluation of the magnitudes of the surface allotments of the surface type with material inclusions can also be made which could, as an example, take the form pursuant to FIG. 5 or 7.

Furthermore, an analysis can be carried out with regard to the locational spatial distribution of the material inclusions across the measurement surface.

FIGS. 3a and 3b represent the measurement result for a surface wherein the illumination angle for FIG. 3b has been changed in a first plane compared to FIG. 3a. Should the angle of illumination be varied in a second plane perpendicular to the first plane, one would receive, for example, the result as depicted in FIG. 3c, in which the corresponding surface areas 51–58 are shifted substantially horizontally as per the orientation of FIG. 3c. Evaluating the horizontal and vertical displacements of individual surface areas (shiftings in the columns and rows) enables a three-dimensional determination of the distribution of material inclusions in the body to be measured.

In the depiction of the image of the detecting means represented in FIG. 3c, the surface is illuminated at a different azimuthal angle relative to that of the results seen in FIG. 3a.

In FIG. 3b, in comparison to FIG. 3a, the individual surface areas 50 of the first surface type, i.e. the material inclusions, have substantially been shifted to higher row numbers within one column. Hence, surface area 52 in column 1 of FIG. 3a covers rows 7–9, while the same surface area in column 1 of FIG. 3b covers row elements 8–10.

An offsetting of the columns due to the changed azimuthal illumination can be noted in FIG. 3c. Surface area 52 has been shifted off the measuring field and is no longer visible in FIG. 3c. Surface area 51, comprising row elements 1–4 in column 3 of FIG. 3a, now comprises as surface area 71 in FIG. 3c, row elements 1–4 in column 2. Surface area 71 in FIG. 3c, resulting from the reflection of a flake or the like is, relative surface section 51 in FIG. 3a, which resulted from the reflection on the same flake, shifted one sensor element to the left in the orientation according to FIG. 3c.

Depending on the difference in angle of illumination, a shifting may also amount to more than just one sensor element. Should two recordings be made at scanning angles which differ greatly from one another, this can make it difficult or almost impossible to allocate the respectively same flakes or metallic particles, etc. to the surface sections of the individual recordings. Although in such a case, an evaluation may also be made as to the statistical distribution across the measurement surface.

From surface areas 53–58 in FIG. 3a, yielding from a number of flakes, corresponding surface areas 73–78 result in FIG. 3c. There is an additional surface area 79 detected in FIG. 3c allotted to a metallic particle, color pigment or flake which had not yet been recorded by detector 16 with the illumination according to FIG. 3a.

An example for the measurement results on the body represented in FIG. 6b is not depicted.

A body in accordance with FIG. 6a or also in accordance with FIG. 6b could yield measurement results in which an allocation of individual flakes from one measurement geometry to the next is not possible, or only possible with great difficulty.

This may be the case, for example, when the illuminating angle for a given surface and flake size, flake form and flake distribution is changed to such a large extent that the detector can no longer log the directional reflection. As is often the case in changes in illuminating angle of 5 degrees or more.

A determination of flake distribution across the surface and also a determination of the distribution given different measurement geometries is, however, possible even when an allotting or "tracing" of individual flakes is not possible at different measurement geometries.

Figure 8:
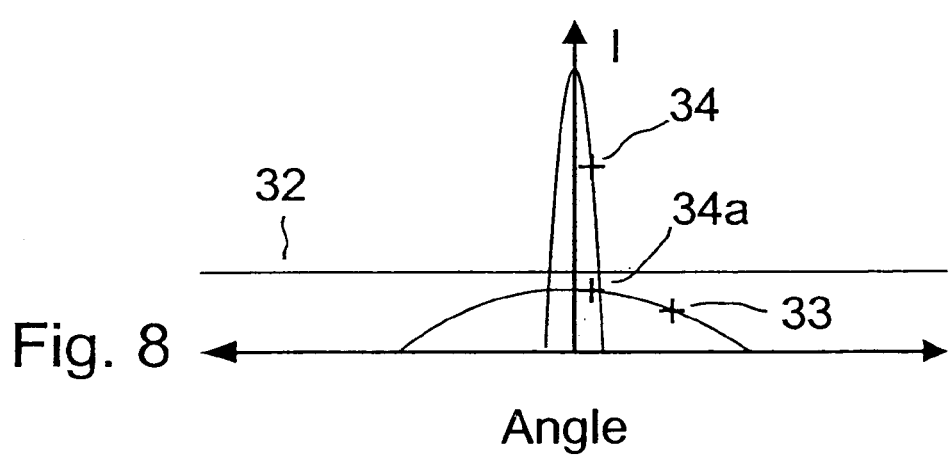
FIG. 8 is a comparison of the intensity of reflection of a material inclusion and a finished surface across the angle of measurement.

The intensity of the measurement result across the sensor elements of a photo detector, or across the angle respectively, is plotted in FIG. 8 since each photo-sensitive element 30 of the photo sensor 16 respectively represents a different angle of measurement.

A distribution of the reflectivity yielded across the scanning angle corresponds to the curve on which measurement 33 is marked. The curve having clearly higher intensity, as indicated by marked measurement value 34, is the curve which yields from specular reflection on a metallic particle at this angle. At the same angle, without the reflecting portion of the metallic particle, only measurement value 34a results, its intensity being clearly lower than the intensity of actual measurement value 34.

It must be noted here in this respect that the entire curve of normal reflectivity (through that of the measurement value 33) comes in below the first predefined threshold 32, while the measurement value for the specular gloss of the metallic particle is clearly above the first threshold. This enables a distinction to be made as regards metallic particle specular gloss and the normal gloss for the layer of finish 82.

When appraising and determining a first surface type for the inlaid metallic or pigment particles 83–86, measurement values may be considered which have higher intensities than the threshold 32, while when appraising the other type of surface, namely the normal finished surface in the present case as depicted, measurement values which are below the first predefined threshold 32 as yielded by normal gloss are considered.

This procedure allows for, on the one hand, determining a parameter for the inlaid particle and, on the other hand, also the evaluating of a parameter for the rest of the finished surface. The separate determination of the visual characteristics increases the precision of the measurement results.

For example, in the measuring of a finished body which has colored metallic particles inlaid into its layer of finish, the wavelength corresponding to the color of the metallic particle will be reflected in greatly amplified measure at certain angles.

A normal determination or evaluation of color will exhibit a distinct over-appraisal of the metallic particle color, while the determination of, on the one hand, visual characteristics for a first type of inlaid inclusion and, on the other hand, parameters for the remaining surface as well as a statistical distribution of the corresponding parameters will lead to clearly improved measurement results. An integral measurement encompassing all pixels can lead to distorted measurement results.

Figure 9A:
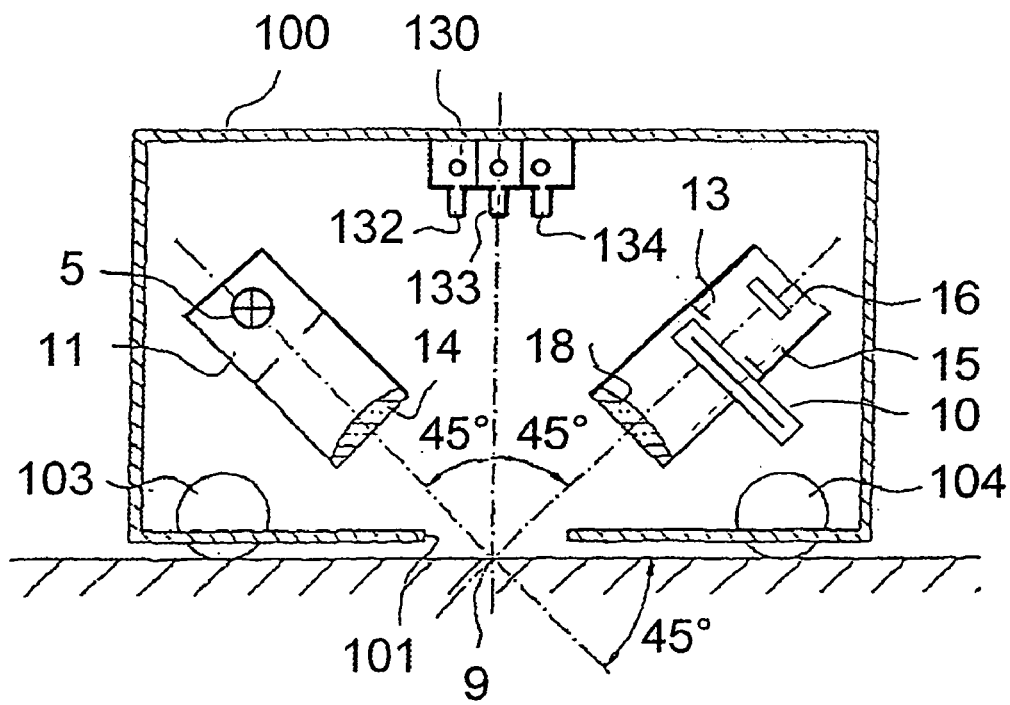
FIG. 9a is a second embodiment of a device according to the present invention.

A further embodiment of an inventive measuring device is represented in FIG. 9a. The same components as in the embodiment according to FIG. 1 have the same reference numerals here.

The light emitted by the first light source 5 hits measurement surface 9 at a 45° angle and the directional reflection is likewise reflected at 45° and directed by a filter wheel 10 to the sensor 16 which is, as in the previous embodiment, configured as a CCD chip.

Filter wheel 10 is partitioned across the angle into eight 45-degree segments, whereby each 45-degree segment comprises a different coloration so as to affect the wavelength characteristic of the transmitted light. Instead of 8 filter segments, 16, 32 or 64 filter segments are also preferred.

During measuring, filter wheel 10 is rotated at given intervals of time or continuously, whereby at least one measurement recording is made with each filter segment. This ensures that the sensor is illuminated with specific ranges of wavelength so that a color of measurement surface 9 can also be ascertained using only one single sensor, CCD chip 16 respectively.

It is important that the filter wheel 10 comprise a sufficiently high enough number of filter segments in order to allow a substantially reliable determination of color. The number of individual filter segments can thus be virtually arbitrary. There should be at least three. Use can also be made of one (or several) filters having continuously tunable filter characteristics. The (spectral) filter characteristics may then be controllable, e.g. electrically.

A further illuminating means 130 is moreover provided in a measuring housing 100 disposed with three separately controllable light-emitting diodes 132, 133 and 134 which emit light at slightly different angles onto the measurement surface 9. Due to the different angles at which the light-emitting diodes 132, 133, 134 are directed to the measurement surface 9, the alignment of material inclusions in the measurement surface can be determined.

In this example, housing 100 is disposed with measuring wheels 103 and 104, whereby at least one of said wheels comprises a rotating angle emitter which emits signals when rolling across the surface corresponding to the relative displacement. This enables a new measurement to be carried out at certain temporal intervals or continuously or at certain spatial intervals when moving across a surface so that a larger measurement area can be acquired. Illumination ensues from an opening 101 in the measuring device onto the surface 9 from which the light is then reflected.

Figure 9B:
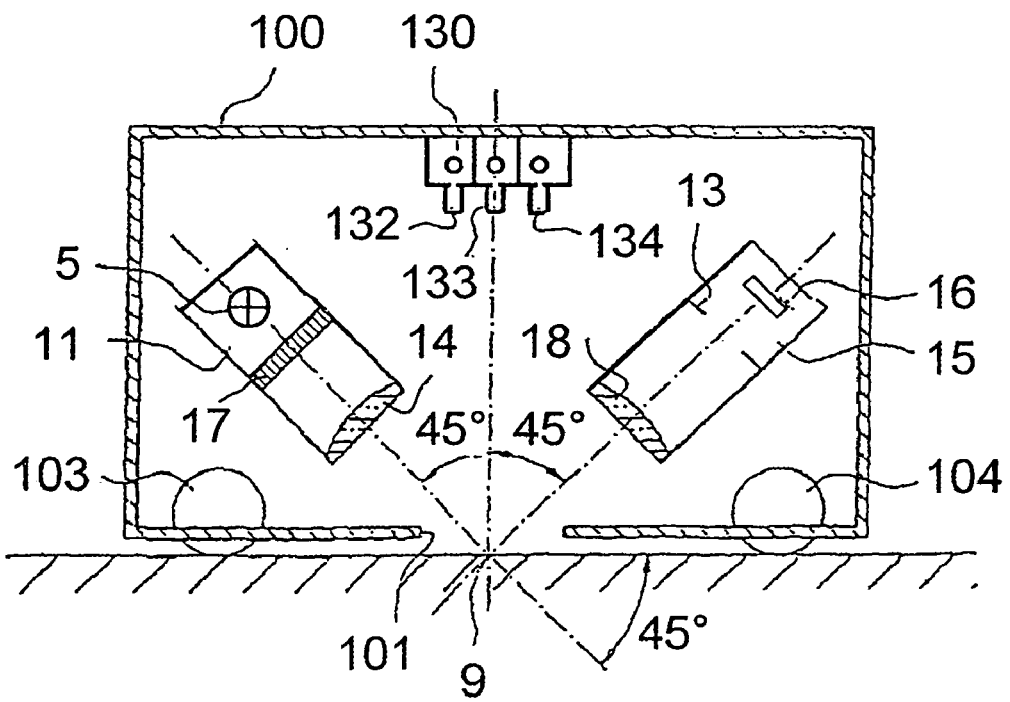
FIG. 9b is a third embodiment of a device according to the present invention.

A further embodiment of an inventive measuring device is represented in FIG. 9b. The same components as in the FIG. 9a embodiment have been given the same reference numerals.

The light emitted by the light source 5 hits the controllable iris 17 which, according to its activation, is switched to transmit as dots, lines, columns or other ranges by the processor 23 while the rest of the area is shadowed. The entire area may also be switched to transmission or shadow. The controllable iris 17 is configured here as an LCD iris.

The transmitted light hits the measurement surface 9 at an approximate angle of 45 degrees, whereby the exact angle is contingent upon the transmittance setting of controllable iris 17. The reflected light is likewise correspondingly reflected at approximately 45 degrees and directed to sensor 16 which, as in the previous embodiment, is configured as a CCD chip. A filter wheel may likewise be provided.

There are further light sources 130 provided in housing 100. The three separately controllable light sources 132, 133 and 134 here have differently colored light-emitting diodes so that a color of the measurement surface can be ascertained upon successive illuminations. Light sources 132, 133 and 134 furthermore each comprise irises and lenses in order to adapt the emitted light to the desired conditions.

Housing 100 has, in this embodiment as well, been disposed with measuring wheels 103 and 104 to determine the relative displacement of the device.

Figure 10:
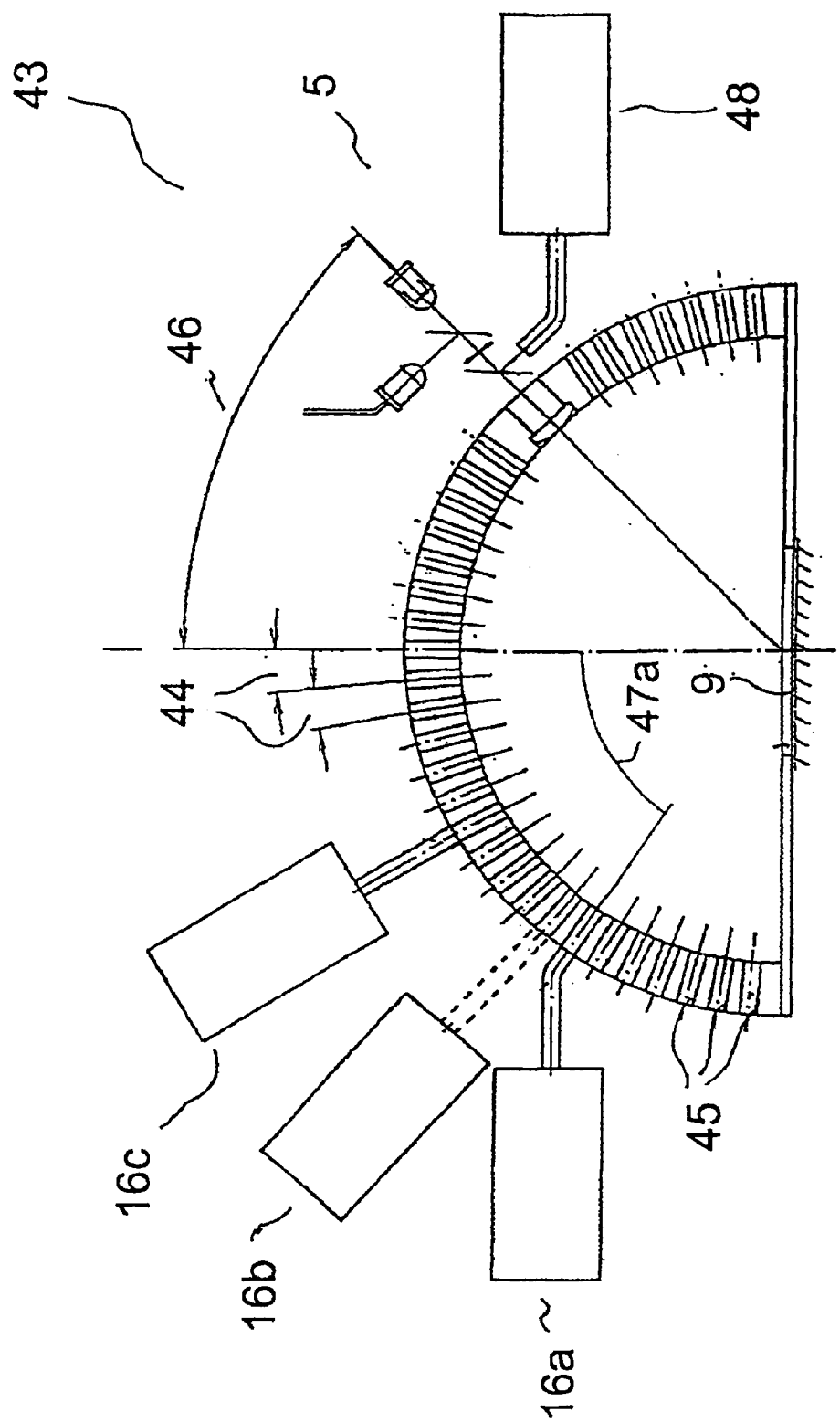
FIG. 10 is a fourth embodiment of a device according to the present invention.

A further embodiment of a device according to the present invention is represented in FIG. 10 in which one illuminating means 5 here comprises two differently colored light-emitting diodes, the emitted light of which is overlapped by beam splitters and directed to the surface to be measured 9. Here as well, only one white light LED may be employed. Similarly, as also in the previous embodiments, a greater number of differently colored LEDs may also be provided.

A small spectrometer 48 serves to control the radiated spectrum and the radiated intensity. The light emitted by the illuminating means is directed to the surface at an angle 46 to the vertical of the measurement surface 9. The embodiment as depicted selects the angle 46 of 45°. Another angle may also be provided. The small spectrometer 48 of this type can also be employed in the embodiments in accordance with FIGS. 1 and 9 in order to control the calculated spectrum.

A plurality of retaining means 45 are arranged in the half-space above the measurement surface 9 which, in the selected embodiment, are each arranged at a set distance of 5 degrees. The retaining means 45 depicted in FIG. 10 are arranged in a plane which extends through illuminating means 5 and measurement surface 9.

Further retaining means 45 are additionally provided in a plane perpendicular thereto analogous to the embodiment according to FIG. 1. The retaining means 45 may also be provided over the entire half-space above measurement surface 9.

Detectors 16a, 16b and 16c are arranged in at least three of the retaining means 45 in a measuring device 43, wherein the at least one detector 16b here is arranged outside of a plane which extends through the detector 16a, the measurement surface 9 and the illuminating means 5.

The multi-dimensional arrangement of the illuminating and sensor means allows for capturing a three-dimensional image of the surface, not merely a one or two-dimensional one.

There is typically a plurality of retaining means provided while only a few detecting means are employed. It is then possible to move one or more detectors from one retaining means to another in the inventive device so that, for example, the measuring angle 47a between the vertical of the measurement surface and detector 16 is adjustable.

The individual detectors 16a, 16b and 16c are likewise configured as CCD chips which are supplied the light received from the surface by light-conducting fiber optics.

It is also possible for a detector, a monochromator respectively, to receive the signal of multiple retaining means 45 successively. The light can be received by light conductors in the retaining means and directed to a monochromator or small spectrometer. In so doing, locational reference may not be maintained. A statistical measure of the flake distribution can be determined from signal distribution and signal height.

A light conductor may, however, also be configured in all embodiments as a location-maintaining optical fiber. For example, the light conductor can contain an optical fiber bundle wherein each individual fiber then represents a certain location or also a certain surface section of the surface. Mapping the signals of the individual fibers in the optical fiber bundle makes it possible to resolve a location. By specific illumination of individual first fiber ends of the fiber bundle, the respectively associated second fiber ends can be detected provided the individual fibers in the bundle are not "sorted." This allows for also making an exact position fix and spatial resolution in the case of optical light conductors having "unordered" optical fiber bundles.

The detector 16 may also be provided on each of the retaining means 45.

In place of detectors, light conductors may also receive the reflected light and convey same to one or more detectors. The individual channels can then be switched in succession and the signals ascertained multiplexedly by a detector. To include a spectral characteristic, a (grid) spectrometer or a filter wheel may be provided in the path of the radiation.

Figure 11:
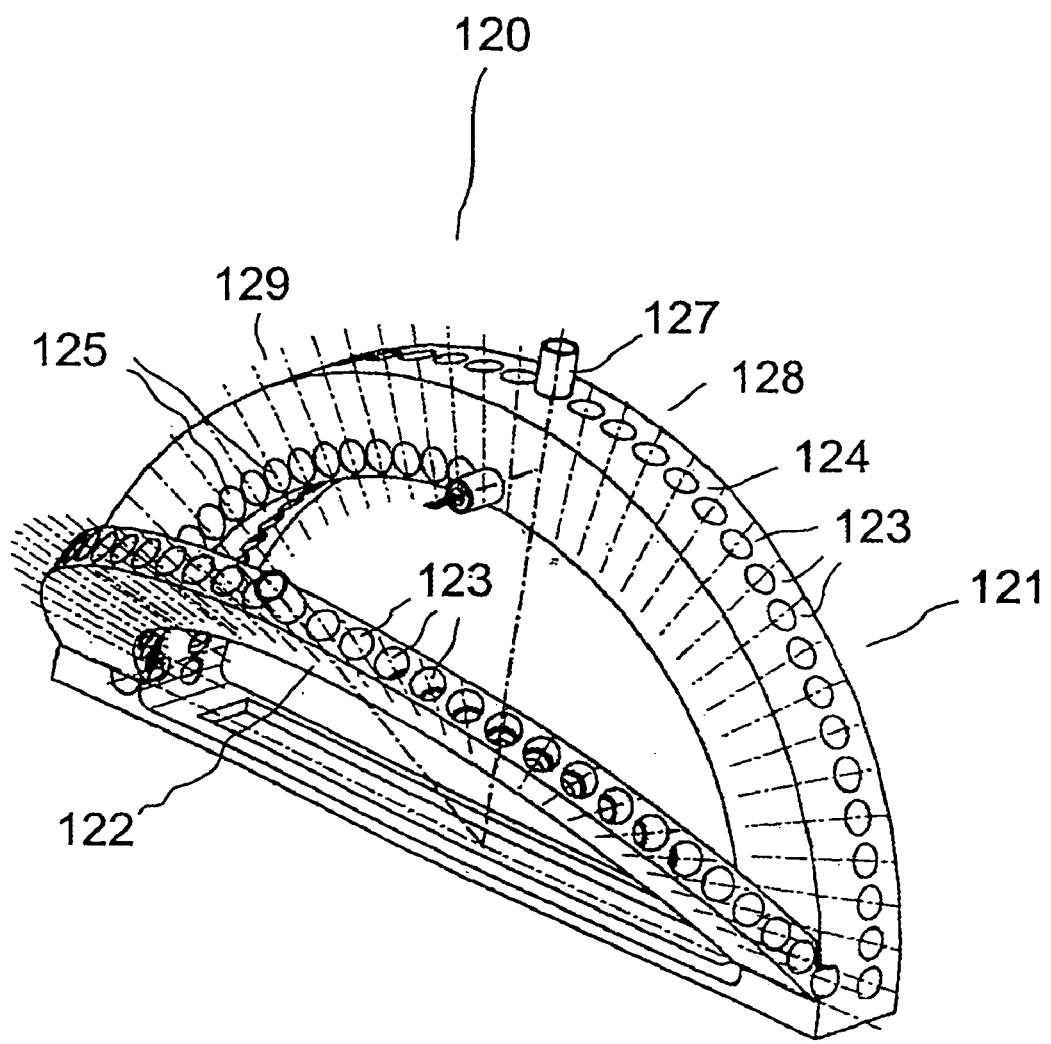
FIG. 11 is a perspective view of a further embodiment of the present invention.

FIG. 11 represents another embodiment of an inventive measuring device 120 in a perspective view. The device 120 exhibits a first subframe or first measuring circle 121, which extends in semicircular fashion over the measurement surface 9. A plurality of retaining means in the form of bore holes 123 are provided in measuring circle 121 into which illuminating or sensor tubus can be introduced.

An illuminating tubus or a sensor tubus may be inserted—as desired—into the individual bore holes 123. A combination tubus may also be employed. A tubus may also be replaced or exchanged for different measurings such that the device according to the present invention achieves a high degree of flexibility.

An angular distance 124 from one of the plurality of holes 123 to an adjacent one of the plurality of holes 123 is fixed in the embodiment as depicted and amounts to 5°. It is however herewith pointed out that other angular spacings are also possible, such as 2.5° or 3° or 10°, etc. It may also be that bore holes 123, respectively receivers for measuring or illuminating tubus are not disposed across the semicircle's entire 180° range of angles but rather only in one or in several ranges of angles.

To determine common visual characteristics such as color, gloss and the like, certain scanning, respectively illumination angles are given which are normally evenly divisible by 5. It is therefore preferred that the bore holes 123 are arranged angularly such that alignment angles to the measurement surface 9 result which are divisible by 5. This is realized in the embodiment in that the retaining means 123 is provided every 5°.

The first measuring circle (or measuring semicircle) 121, extending vertically over measurement surface 9, has a first segment 128 and a second segment 129, whereby in the selected embodiment, each of the segments extends across a 90° range of angles.

In first and second segments 128 and 129, the bore holes 123 are so aligned that the respective central axes of the bore holes 123 are directed to the center of the measurement surface 9.

Additional receivers, respectively a plurality of bore holes 125 are provided in second segment 129, the respective axes of which extend parallel to the measurement surface 9, respectively perpendicular to bore holes 123.

The inventive device 120 furthermore comprises a second measuring circle 122, likewise disposed with receiving means or bore holes 123 which are arranged here as well at an angular spacing 124 of 5° to one another. As with the first measuring circle, the central axes of holes 123 in the second measuring circle are also directed to the center of measurement surface 9.

In contrast to the first measuring circle 121, the second measuring circle 122 is not aligned in a plane perpendicular to the measurement surface 9, but rather at an angle 126 to the vertical of the measurement surface.

The angle 125 amounts to 45° in the embodiment but it may also be 10°, 15°, 20°, 25°, 30°, 60° or 75°. Furthermore, the angle 126 of the second measuring circle 122 can be adjustable over fixed gradations or continuously.

For performing measurements, every receiver 123 of the first segment 128 of the first measuring circle 121 and every bore 123 of the second measuring circle of the measuring device 120 can be fitted with an illuminating tubus and/or with a sensor tubus.

In the second segment 129 of the first measuring circle 121, illuminating tubus, sensor tubus, measuring tubus and/or combination tubus may be alternatively employed in the receivers 123 and 125.

Figure 12:
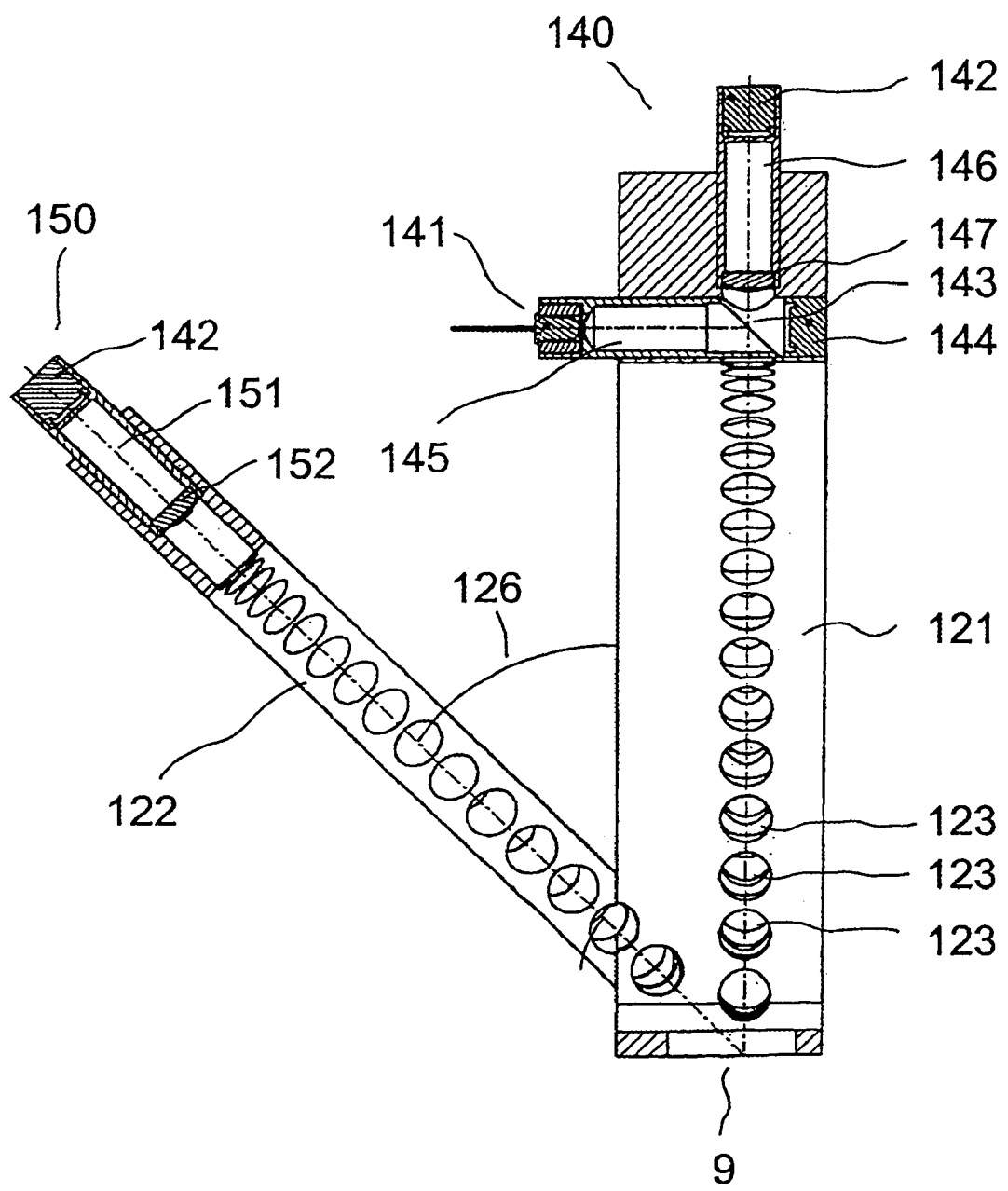
FIG. 12 is a side view of the device pursuant to FIG. 11.

The measuring tubus, respectively combination tubus 140 visible in FIG. 12 comprises a sensor tubus 146 having a sensor 142 and a lens 147. An illuminating tubus 145 having a light source 141 is furthermore provided. Light source 141 in the embodiment is a so-called white light-emitting diode. It is also possible to make use of other light sources or two or three or more different colored light-emitting diodes in illuminating tubus 145, the-light of which is then overlapped spatially.

The optical axes of the illuminating and sensor tubus 145 and 146 intersect at a beam splitter 143 of the combination tubus at a 90° arrangement to one another.

The light emitted from the light-emitting diode 141 in the embodiment hits beam splitter 143 at 45°. A portion of the light emitted from light-emitting diode 141 is transmitted by beam splitter 143 and impinges a reference measuring cell 144 so that the intensity of the light-emitting diode 141 is controllable.

It is also possible that the reference signal is directed to a spectrometer or the like by an optical fiber so that not only the intensity but also the spectral distribution of the light emitted by light-emitting diode 141 will be determined.

The spectrometer then not only detects the light of one light-emitting diode 141 but, e.g. through use of an optical multiplexer, the light of a plurality of fibers conveying the light of light sources 141.

A further portion of the light emitted from light source 141 is reflected by the beam splitter 143. The beam splitter 143 arranged at 45° reflects this portion to the measurement surface 9 along the optical axis of bore hole 123.

The incident light there is reflected to the half-space above measurement surface 9. A portion of this light is reflected back onto itself, reaches combination tubus 140 and in turn impinges beam splitter 143.

A portion of the returning light is now in turn transmitted through beam splitter 143 and, travelling along the optical axis of sensor tubus 146, reaches lens 147 to impinge sensor 142.

Sensor 142 is configured as a CCD sensor and detects the impinging light's distribution of intensity on the individual surface elements 30.

Sensor(s) 142 can, contingent upon embodiment, also integrally detect the light received or also only integrally over the respective sensor surface.

For color measurements, sensor 142 can be configured as a color CCD sensor. It is likewise possible that the filter wheel means 10 is provided in the path of radiation in sensor tubus 146 as was described with respect to the embodiment according to FIG. 9. The filter wheel means 10 disposed in measuring tubus 146 allows a reliable determination of the color of the light reflected by the measurement surface 9.

It is also possible to provide the beam splitter 143 and color filter in sensor 142, which separates the light impinging the sensor and splits it up into its color components. Separate sensor elements allow for determining the color of the measurement surface 9.

The measuring or combination tubus 142 is highly advantageous because it is this combination tubus which allows for illuminating the surface and simultaneously detecting the measurement result at the same angle.

The light impinging sensor tubus 146 of combination tubus 140 may also be directed to a separate sensor by an optical light conductor which, for example, conveys the signals from other sensor tubus over a plurality of optical fibers in succession.

It is also possible that the receivers 123 in the first segment 128 are configured like the receivers in the second segment 129 and that the additional receivers, respectively the bore holes 125, are also provided in the first segment of the first measuring circle 121 so that combination tubus 140 can be inserted into the first and second segments.

Should combination tubus be utilized at the same respective angle to the vertical of the measurement surface, both illuminating tubus 141 of both combination tubus 140 could radiate light to the surface simultaneously and the directly reflected light could be simultaneously detected in the measuring tubus 142 of the respective other combination tubus 140.

A second measuring circle 122 is disposed with bore holes 123 which are likewise construed to receive measuring tubus or illuminating tubus. In the depicted embodiment, measuring tubus 151 are provided in receivers 123 of the second measuring circle 122 which correspond to the configuration of measuring tubus 146 of the combination tubus. A sensor 142 and a lens 152 is likewise provided.

Due to the angle 126 at which the second measuring circle 122 is aligned relative the vertical of the measurement surface 9, the measurement surface of a body to be measured can be measured three-dimensionally.

Evaluation of the measurement results is performed as is described with respect to FIGS. 1–10.

In connection hereto, the applicant would like to point out that they reserve the right to also apply for protection separately for the three-dimensional arrangement of measuring and illuminating means, combination tubus respectively, without any ensuing statistical evaluation.

In such an arrangement, the features that there is at least one predefined threshold provided in a memory means; that a measurement value of a sensor means is allotted to a first surface type when same exceeds the first threshold; and that at least one statistical parameter is determined which characterizes the first surface type are omitted.

Such an arrangement could instead encompass the features that at least a second detector means and/or at least a second illuminating means is arranged outside of a first measuring plane which extends through a first illuminating mea, a first detecting means and the measurement surface. This would enable multi-dimensional measurements.

The applicant further reserves the right to a further arrangement in which an inventive device for the determination of the properties of reflective bodies comprises the following:

at least one measuring means which includes at least one illuminating means and at least one detecting means;

whereby light can be emitted to the measurement surface by the at least one illuminating means;

wherein at least a portion of the light reflected by the measurement surface can be logged by the at least one detecting means;

at least one of the at least one detecting means includes a plurality of light-sensitive sensor means, whereby substantially each of the sensor means can output a respective measurement value which is characteristic for the light received by each respective sensor means;

at least one memory means;

at least one controlling means for controlling the measurement sequence which includes at least one processing means; wherein a measuring procedure can be controlled by the controlling means; and wherein at least one of the at least one measuring means is configured such that the illuminating means of the measuring means directs light at a predetermined angle onto the measurement surface and that the detecting means of the measuring means receives the radiation reflected from the measurement surface at substantially the same predetermined angle.

The features omitted here are that of providing a first threshold and that a measurement value of a sensor means is allotted to a first surface type when same exceeds the first threshold; and that a statistical parameter is determinable which characterizes the first surface type. In lieu thereof, features directed to the measuring means were included according to which at least one measuring means includes at least one illuminating means and at least one detecting means.

It is although then also possible that measuring devices as described in the embodiments only determine integral parameters of surfaces to be measured. Such a determination is sufficient for many surfaces.

What is claimed is:

1. A device for determining the properties of reflective bodies and especially of heterogeneous reflective bodies having:

at least one illuminating means which emits light onto a measurement surface;

at least one detecting means for recording the light reflected from said measurement surface;

wherein at least one of said at least one detecting means comprises a plurality of light-sensitive sensor means, and whereby a measurement value is issuable from substantially each of said sensor means which is characteristic of the light received by each respective sensor means;

at least one memory means, in which at least one first predefined threshold is provided;

at least one controlling means for controlling the measurement sequence which comprises at least one processing means;

whereby a measurement sequence is controllable by said controlling means such that a measurement value of a sensor means is allocated to a first surface type when same exceeds said first threshold;

wherein at least two of said sensor means are respectively associated with different locations to be measured on said measurement surface; and wherein said controlling means is configured for issuing at least one statistical parameter which characterizes said first surface type.

2. The device according to claim 1, wherein a second predefined threshold is provided in said at least one memory means.

3. The device according to claim 2, wherein a measurement value is allocated to a second surface type when same falls below said second threshold.

4. The device according to claim 2, wherein said second predefined threshold is less than said first predefined threshold.

5. The device according to claim 2, wherein at least a third threshold and a third surface type are provided and measurement values are allocatable to said surface type.

6. The device according to claim 1, wherein the sensor means of at least one detecting means is arranged in rows and columns.

7. The device according to claim 1, wherein at least one statistical parameter is derivable as to the spatial distribution of at least one surface type across said measurement surface.

8. The device according to claim 7, wherein from the surface sections of at least one surface type, at least one statistical parameter for the spatial distribution of said surface sections of said at least one surface type on the measurement surface is derivable.

9. The device according to claim 1, wherein a plurality of surface sections are derivable, whereby measurement values of neighboring sensor means having the same surface type are allocated to the same surface section.

10. The device according to claim 9, wherein at least one statistical parameter is derivable from the surface sections of at least one surface type for the surface section size distribution for said surface type.

11. The device according to claim 1, wherein a property of the imaging optics of at least one detecting means is modifiable so that a section of said measurement surface is depictable at an altered scale.

12. The device according to claim 1, wherein at least one visual characteristic is determinable which characterizes at least one visual property of said measurement surface, whereby said visual property is taken from a group of parameters which includes gloss, color, orange peel, haze, distinctness of image (DOI) and the like.

13. The device according to claim 1, wherein at least two different visual characteristics are determinable for said measurement surface.

14. The device according to claim 1, wherein at least one visual characteristic is determinable for at least one surface section of at least one surface type.

15. The device according to claim 1, wherein at least one visual characteristic is determinable for at least one surface type.

16. The device according to claim 1, wherein the sum of the total number of detecting means and the total number of illuminating means amounts to at least three.

17. The device according to claim 16, wherein at least one of said detecting means and of said illuminating means is arranged outside of a first measuring plane extending through a first illuminating means, a first detecting means and the measurement surface.

18. The device according to claim 16, wherein at least one of said detecting means and of said illuminating means is arranged outside of a first measuring plane extending through a first illuminating means, a first detecting means and the measurement surface at a predefined azimuthal angle to said first measuring plane.

19. The device according to claim 16, wherein at least one parameter is determinable respectively for at least two different measurement geometries, wherein a measurement geometry is characteristic of the respective illuminating angle and respective measuring angle.

20. The device according to claim 1, wherein at least three detecting means are provided.

21. The device according to claim 1, wherein at least three illuminating means are provided.

22. The device according to claim 1, wherein each illuminating means and each detecting means are respectively arranged substantially at a predetermined angle of height to said measurement surface.

23. The device according to claim 1, wherein at least one measuring device is provided which comprises at least one illuminating means and at least one detecting means.

24. The device according to claim 23, wherein said illuminating means of said measuring device directs radiation at a predefined measuring device angle onto said measurement surface and said detecting means receives the reflected radiation from said measurement surface at substantially this same predefined measuring device angle.

25. The device according to claim 23, wherein said measuring device comprises at least one beam splitter.

26. The device according to claim 25, wherein said beam splitter of said measuring device diverts radiation emitted from said illuminating means to said measurement surface.

27. The device according to claim 25, wherein said beam splitter of said measuring device allows radiation received from said measurement surface to pass through to said detecting means.

28. The device according to claim 23, wherein at least one detecting means is provided which controls the light emitted by at least one illuminating means.

29. The device according to claim 1, wherein at least one portion of said illuminating means can be triggered substantially successively during a measurement procedure in such a manner that the respective light emitted by same is measurable separately by the detecting means.

30. The device according to claim 1, wherein at least one portion of said illuminating means can be triggered substantially simultaneously during a measurement procedure in such a manner that the light emitted by same can be measured simultaneously by the detecting means.

31. The device according to claim 1, wherein the angle of touchdown of said device on said measurement surface is variable.

32. The device according to claim 31, wherein said angle of touchdown can be varied at least at predetermined gradiations.

33. The device according to claim 31 wherein said angle of touchdown is measurable.

34. The device according to claim 1, wherein at least one statistical parameter respectively is derivable for at least two measurement geometries.

35. The device according to claim 1, wherein a statistical distribution of at least one statistical parameter and visual characteristic of at least one surface type is derivable for a plurality of measurement geometries.

36. The device according to claim 1, wherein at least two illuminating means are provided which are arranged substantially in a plane perpendicular to said measurement surface.

37. The device according to claim 36, wherein at least one illuminating means is provided which is arranged substantially outside of a plane perpendicular to said measurement surface, whereby said plane extends vertical to said measurement surface through said measurement surface and a detecting means.

38. The device according to claim 1, wherein at least two detecting means are provided which are arranged substantially in a plane perpendicular to said measurement surface.

39. The device according to claim 1, wherein at least one detecting means is provided which is arranged substantially outside of a plane perpendicular to said measurement surface, whereby said plane extends vertical to said measurement surface through said measurement surface and an illuminating means.

40. The device according to claim 1, wherein at least the sensor means of one detecting means are arranged on one common substrate, whereby said detecting means is configured as a CCD chip.

41. The device according to claim 1, wherein at least one detecting means is configured as a color CCD chip.

42. The device according to claim 1, wherein at least one iris means is arranged in the path of radiation between at least one illuminating means and at least one detecting means.

43. The device according to claim 42, wherein said at least one iris means is arranged between one illuminating means and the measurement surface.

44. The device according to claim 42, wherein at least one of said at least one iris means is arranged between the measurement surface and at least one detecting means.

45. The device according to claim 42, wherein at least one of said at least one iris means comprises a controllable iris aperture.

46. The device according to claim 45, wherein said controllable iris means is one taken from a group of iris means which includes those exhibiting at least one controllable aperture of a dotted, slotted, linearly-shaped and rounded profile and other similar profiles.

47. The device according to claim 45, wherein said iris means is configured as an LCD iris means.

48. The device according to claim 1, wherein at least one illuminating means comprises at least one light source which is taken from among a group of light sources which includes light-emitting diodes (LED), laser or thermal sources of radiation such as halogen, krypton and incandescent radiation, and the like.

49. The device according to claim 1, wherein the frequency of the light emitted by at least one illuminating means is controllable, whereby a color of said emitted light can be modified.

50. The device according to claim 1, wherein at least one illuminating means comprises a continuously tunable laser.

51. The device according to claim 1, wherein at least one filtering means is arranged in the path of radiation between at least one illuminating means and at least one detecting means.

52. The device according to claim 51, wherein a spectral characteristic of said filtering means may be modified.

53. The device according to claim 51, wherein said at least one filtering means comprises a filter wheel device which exhibits different spectral characteristics across its periphery and which is rotatable.

54. The device according to claim 1, wherein at least one detecting means comprises sensor means of spectrally different sensitivities.

55. The device according to claim 54, wherein at least three sensor means of spectrally different sensitivities are provided in at least one detecting means.

56. The device according to claim 55, wherein said at least three sensor means of spectrally differing sensitivities measure light from substantially the same measurement point on said measurement surface.

57. The device according to claim 1, wherein said device is displaceable relative to said measurement surface and at least one path measuring means is provided which quantitatively records said relative displacement.

58. The device according to claim 57, wherein said path measuring means comprises at least one measuring wheel which sets upon the surface to be measured during measurement and rotates during said relative displacement.

59. The device according to claim 57, wherein a frame device is provided on which said path measuring means is arranged.

60. The device according to claim 57, wherein said path measuring means comprises at least one rotating angle emitter which emits an electrical signal which is representative of said relative displacement.

61. The device according to claim 57, wherein said relative displacement allows for locationally-contingent measurements to be performed and that at least one of said visual statistical parameters is obtainable in accordance with spatial location.

62. The device according to claim 1, wherein the measurement surface on said body to be measured is selectable upon changing of the system angle.

63. The device according to claim 1, wherein a supporting device is provided on which said illuminating means and detecting means are arranged and a robot arm device is provided for the automatic guiding of said supporting device along a measurement surface.

64. The device according to claim 1, wherein at least one detecting means and at least one illuminating means are arranged such that at least one visual transmittance property of said measurement surface is determinable.

65. The device according to claim 64, wherein a spectral filtering means is provided on at least one illuminating means which approaches the spectrum emitted in a predetermined spectral distribution.

66. The device according to claim 1, wherein at least one detecting means comprises at least one spectrometer device so that a spectral characteristic of the received light is ascertainable.

67. The device according to claim 1, wherein at lest one retaining means is provided which serves in the receiving of an optical device, whereby said optical device is taken from among a group of optical devices including detecting means, illuminating means, measuring means and the like.

68. The device according to claim 67, wherein a plurality of retaining means are provided in at least one measuring plane which each respectively exhibit the same angular separation to one another.

69. The device according to claim 68, wherein said angular separation of said retaining means is taken from among a group including angular separations of 1°, 2°, 2.5°, 3°, 4°, 5°, 10°, 15°.

70. The device according to claim 67, wherein a plurality of retaining means are provided in at least one second measuring plane.

71. A process for determining the properties of reflective bodies and especially of heterogeneous reflective bodies with a device comprising:
- at least one illuminating means which radiates light onto a measurement surface;
- at least one detecting means which records said light reflected from said measurement surface; whereby at least one of said at least one detecting means comprises a plurality of light-sensitive sensor means, with substantially each of said sensor means issuing a respective measurement value which is characteristic of the light received by said respective sensor means;
- at least one memory means in which at least one first predefined threshold is provided;
- at least one controlling means which comprises at least one processing means and which controls the measurement sequence;
- wherein at least two of said sensor means are respectively associated with different locations to be measured on said measurement surface;
- whereby the process encompasses at least the following steps:
  a) directing of said at least one illuminating means to illuminate said measurement surface;
  b) directing of said sensor means of at least one detecting means to record the measurement signals of said sensor means of said at least one detecting means and to convert same into measurement reference values;
  c) storing of at least a portion of the measurement values recorded;
  d) comparing the magnitude of each measurement reference value with a first threshold stored in the memory means in order to allocate each measurement value to a first surface type should said measurement value be greater than said first threshold; and
  e) issuing of at least one statistical parameter which characterizes said first surface type, whereby said controlling means is configured for issuing said at least one statistical parameter which characterizes said first type.

72. The process according to claim 71, wherein the number of measurement values for the first surface type is determined and set in relation to the number of measurement values as a whole.

73. The process according to claim 71, wherein at least one second threshold is provided in said at least one memory means and measurement values which are lower than said second threshold are allocated to a second surface type.

74. The process according to claim 71 including a device which records an image of the measurement surface with at least one detecting means, wherein at least one statistical parameter is derived for the statistical spatial distribution of said first surface type on said measurement surface.

75. The process according to claim 71, wherein the surface area for at least one surface type is derived, whereby the surface of an extension area is determined through the measurement values of neighboring sensor means of the same surface type.

76. The process according to claim 75, wherein a size figure is determined for the size of the individual surface areas and at least one statistical parameter is derived which is characteristic for a statistical distribution of size for the surface areas of at least one surface type.

77. The process according to claim 75, wherein at least one form figure is determined for the form of the individual surface areas and preferably at least one statistical form parameter is derived which is characteristic for a statistical distribution of form for the surface areas of at least one surface type.

78. The process according to claim 71, wherein the individual procedural steps are performed for at least two measurement geometries, whereby a measurement geometry is defined by one illuminating angle to the measurement surface and one detecting angle to said measurement surface.

79. The process according to claim 78, wherein at least one distribution of at least one statistical parameter is derivable from said measurement geometry.

80. The process according to claim 71, wherein measurement values of said first surface type are allocated to a first type of material inclusion for the body to be measured, and a statistical parameter for the spatial distribution of said first type of material inclusion across the measurement surface is determined.

81. The process according to claim 80, wherein a comparison of said surface section from at least three differing measurement geometries allows for the deriving of a characteristic measure for a three-dimensional form of said first material inclusion, wherein each of said at least three differing measurement geometries is defined by the illumination angle onto said measurement device.

82. The process according to claim 80, wherein a comparison of said surface section from at least three differing measurement geometries allows for the deriving of a characteristic measure for a three-dimensional position of said first material inclusion.

83. The process according to claim 80, wherein at least one characteristic visual parameter is determined for at least one surface type in that only measurement values of the respective surface type are considered when determining characteristic visual parameters.

* * * * *